(12) United States Patent
Shah et al.

(10) Patent No.: US 11,529,053 B2
(45) Date of Patent: Dec. 20, 2022

(54) SYSTEM AND METHOD FOR DISEASE RISK ASSESSMENT AND TREATMENT

(71) Applicant: PercuSense, Inc., Valencia, CA (US)

(72) Inventors: Rajiv Shah, Rancho Palos Verdes, CA (US); Bradley C Liang, Bloomfield Hills, MI (US); Ellen Messer, Pasadena, CA (US); Katherine Wolfe, Mississauga (CA)

(73) Assignee: PercuSense, Inc., Valencia, CA (US)

( * ) Notice: Subject to any disclaimer, the term of this patent is extended or adjusted under 35 U.S.C. 154(b) by 0 days.

(21) Appl. No.: 16/054,649

(22) Filed: Aug. 3, 2018

(65) Prior Publication Data

US 2019/0183339 A1 Jun. 20, 2019

Related U.S. Application Data

(60) Provisional application No. 62/608,492, filed on Dec. 20, 2017.

(51) Int. Cl.
*A61B 5/00* (2006.01)
*A61B 5/145* (2006.01)
(Continued)

(52) U.S. Cl.
CPC .......... *A61B 5/0031* (2013.01); *A61B 5/0006* (2013.01); *A61B 5/0205* (2013.01); *A61B 5/02444* (2013.01); *A61B 5/14503* (2013.01); *A61B 5/14542* (2013.01); *A61B 5/25* (2021.01); *A61B 5/7275* (2013.01); *G16H 50/30* (2018.01);
(Continued)

(58) Field of Classification Search
CPC ... A61B 5/0006; A61B 5/0031; A61B 5/0205; A61B 5/02444; A61B 5/0408; A61B 5/042; A61B 5/0452; A61B 5/0537; A61B 5/14503; A61B 5/14532; A61B 5/14542; A61B 5/14546; A61B 5/14865; A61B 5/4878; A61B 5/685; A61B 5/7275; A61B 2562/0219; A61B 2562/04;
(Continued)

(56) References Cited

U.S. PATENT DOCUMENTS

| 2010/0312188 A1* | 12/2010 | Robertson | A61B 5/0006 604/156 |
| 2011/0021889 A1* | 1/2011 | Hoss | A61B 5/7221 600/310 |

(Continued)

FOREIGN PATENT DOCUMENTS

WO     2017/196576     11/2017

OTHER PUBLICATIONS

Simon Lebech Cichosz et al: "Combining Information of Automatic Modulation and CGM Measurements Enables Prediction and Improves Detection of Spontaneous Hypoglyemic Events", Journal of Diabetes Science and Technology, Sep. 12, 2014, pp. 132-137, XP055566286, Los Angeles, CA DOI: 10.1177/1932296814549830.

*Primary Examiner* — Carl H Layno
*Assistant Examiner* — Jane C Kalinock
(74) *Attorney, Agent, or Firm* — PercuSense, Inc.

(57) ABSTRACT

A biosensor assembly that measures multiple physical parameters is disclosed. The biosensor assembly includes a first implantable probe and a first skin contacting electrode. Wherein a first physiological parameter is measured between the first implantable probe and the first skin contactable electrode.

10 Claims, 17 Drawing Sheets

(51) Int. Cl.
*A61B 5/024* (2006.01)
*A61B 5/0408* (2006.01)
*A61B 5/0205* (2006.01)
*G16H 50/30* (2018.01)
*A61B 5/25* (2021.01)
A61B 5/0537 (2021.01)
A61B 5/1486 (2006.01)
A61B 5/283 (2021.01)
A61B 5/349 (2021.01)

(52) U.S. Cl.
CPC ......... *A61B 5/0537* (2013.01); *A61B 5/14532* (2013.01); *A61B 5/14546* (2013.01); *A61B 5/14865* (2013.01); *A61B 5/283* (2021.01); *A61B 5/349* (2021.01); *A61B 5/4878* (2013.01); *A61B 5/685* (2013.01); *A61B 2562/0219* (2013.01); *A61B 2562/04* (2013.01); *A61B 2562/06* (2013.01); *A61B 2562/16* (2013.01)

(58) Field of Classification Search
CPC ............ A61B 2562/06; A61B 2562/16; A61B 2560/0462; G16H 50/30
USPC .......................................................... 600/301
See application file for complete search history.

(56) References Cited

U.S. PATENT DOCUMENTS

| | | | |
|---|---|---|---|
| 2013/0313130 A1* | 11/2013 | Little | A61B 5/14532 205/792 |
| 2016/0331290 A1* | 11/2016 | Oh | A61B 5/0538 |
| 2017/0027514 A1* | 2/2017 | Biederman | A61B 5/1451 |
| 2017/0086713 A1* | 3/2017 | Pushpala | A61B 5/7278 |
| 2018/0014742 A1* | 1/2018 | Iwawaki | A61B 5/02 |
| 2020/0315503 A1* | 10/2020 | Heikenfeld | A61B 5/14546 |

* cited by examiner

Interactive Mode Screen

Summary Screen (Notification)

Notes and Clinician Contact Screen

Real-time Data Screen

SYSTEM AND METHOD FOR DISEASE RISK ASSESSMENT AND TREATMENT

RELATED APPLICATIONS

This application claims the benefit of U.S. provisional application No. 62/608,492, filed Dec. 20, 2017. The application listed above are hereby incorporated by reference in their entireties for all purposes.

FIELD OF THE INVENTION

The invention generally relates to systems and methods for real time monitoring of physiological parameters to enable diagnosis and monitoring of disease progression including risk assessment, diagnosis, treatment and monitoring. More specifically, the invention relates to the use of sensors and related electronics in conjunction with algorithms and software for the early identification and warning before the onset of various disease states.

BACKGROUND OF THE INVENTION

Detecting changes in perfusion is critical to ensure adequate tissue oxygenation and perfusion. Traditional methods of detecting physiological changes of perfusion include measurements of blood pressure, heart rates, urine output, serum levels of lactate, mixed venous oxygen saturation and central venous saturation. However, apart from changes in inspired oxygen concentration, in general, there is a poor relationship between arterial oxygen and partial pressure of oxygen within the interstitial space of a particular tissue. This disparity emphasizes the important clinical and physiological lesson that normal arterial values should not be used as a replacement or surrogate for satisfactory oxygenation at the tissue level.

Real-time monitoring of oxygen within tissue provides insight to changes in the microcirculation of a subject. Because many disease states or other physical conditions affect microcirculation understanding the pathophysiological development of various conditions can enable clinicians to diagnose, treat, and monitor efficacy of treatment based on real-time monitoring of various parameters associated with microcirculation. For example, patients with acutely decompensated heart failure have significantly decreased tissue oxygenation that is lower than those found in a stable outpatient population. Accordingly, measurement of subcutaneous tissue oxygen may enable clinicians to diagnose and treat heart failure more effectively.

The claimed invention seeks to address timely and cost effective methods and systems to diagnose heart failure and other conditions that are detectable via pathophysiological changes in microcirculation. In many examples discussed below multiple analytes and physical parameters are monitored. While embodiments and examples may be related to particular analytes and physical parameters, the scope of the disclosure and claims should not be construed to be limited to the specifically addressed analytes and parameters. Rather it should be recognized that additional or other analytes and physical parameters can be monitored to assist in the detection and diagnosis of heart failure.

BRIEF SUMMARY OF THE INVENTION

In one embodiment a biosensor assembly that measures multiple physical parameters is disclosed. The biosensor assembly includes a first implantable probe and a first skin contacting electrode. Wherein a first physiological parameter is measured between the first implantable probe and the first skin contactable electrode.

Other features and advantages of the invention will become apparent from the following detailed description, taken in conjunction with the accompanying drawings that illustrate, by way of example, various features of embodiments of the invention.

DETAILED DESCRIPTION

Figure 1:
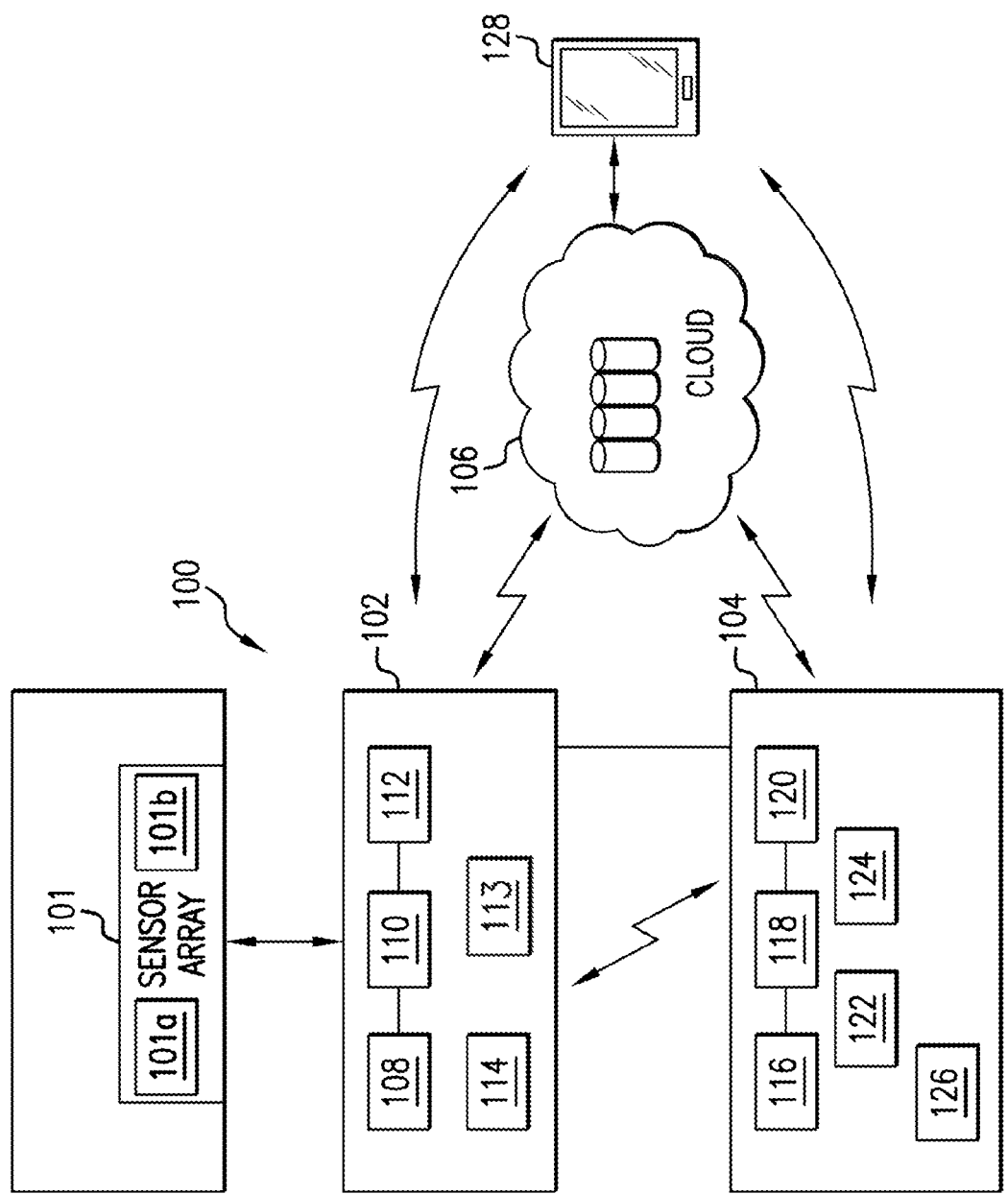
FIG. 1 is an exemplary block diagram showing components within a system to determine a risk score of developing heart failure, in accordance with embodiments of the invention.

Simultaneous continuous or periodic measurement of physical parameters and chemical entities as a means of measuring disease progression or inflection that requires timely clinical intervention can be extended to a multitude of disease states and may include multiple measurement modalities. The design of such medical monitoring systems requires an understanding of the pathophysiological processes associated with a particular illness or disease. From this basic understanding, a number of small molecules, biological markers of disease, and physiological measures with high diagnostic and prognostic value for a particular disease and/or condition can be identified. Sensors that rely on physical, electrochemical, and optical transducers can be functionalized to directly or indirectly measure the small molecules, biological markers, and physiological measures associated with a specific disease. Advanced manufacturing techniques can then be used to integrate the sensors in question into a multi-analyte or multi-parameter that can be deployed invasively or noninvasively within a target population. Software algorithms that combine an understanding of disease, artificial intelligence, and machine learning can be embedded in the instrumentation or systems that power and acquires data from a disease specific multi-parameter sensor to assess the cellular and/or systemic progression of condition or disease. Configurable alerts and alarms associated with the medical monitoring system can be communicated through wired and wireless methods to enable timely therapeutic intervention in order to derive the benefits of proactive disease or illness management.

Disclosed below is a robust system that performs real-time simultaneous continuous monitoring of specific risk metrics to generate a risk score for heart failure. The risk score for heart failure is determined using risk metrics based on data obtained from (i) sensors placed in contact or implanted within a subject and/or (ii) other external input available on the subject (such as electronic medical records, test data from hospital/clinic measurements where the subject is being evaluated, or has been evaluated previously, for a medical condition). Risk metrics based on sensor data can be based on continuous and substantially real-time monitoring of analytes and physiological parameters relevant to heart failure. In one embodiment, the risk metrics include, but are not limited to analytes such as, tissue oxygen, redox potential (ORP) and reactive oxygen species (ROS) along with physical parameters such as, but not limited to heart rate, electrocardiography, and edema. Detectable changes in those risk metrics can be indicative of an increasing risk of heart failure or further progression of heart failure because low tissue oxygenation may be indicative of inefficient oxygen transfer via the circulatory system and an increase in ROS may be suggestive of irregular stress and/or cellular death.

In a simple embodiment the heart failure risk score is determined based on a sum of normalized primary inputs, where primary inputs include input like ECG data along with sensed or measured concentrations of analytes such as, but not limited to, tissue oxygen ORP and ROS. A more refined heart failure risk score is determined by incorporating secondary inputs, which are risk metrics that are calculated based on primary inputs. Examples of secondary inputs include, but are not limited to rates of change of glucose, tissue oxygen, ROS, ORP, and lactate. In a variation of this embodiment, the risk score additionally incorporates looking at measured inputs over time differently. For example, rather than using the same time window for all evaluations, each analyte or metric is examined at a preferred frequency. Relative weighting factors can also be applied to either or both primary and secondary inputs to emphasize or deemphasize particular risk metrics when determining a risk score.

The system is configurable for use in a variety of environments including, but not limited to ambulatory patient monitoring and remote monitoring, where each mode may be further supplemented with a feedback/treatment mode. In an ambulatory patient monitoring environment, the risk score and changes to the risk score over time enables both automated evaluation if a patient may be trending toward developing heart failure or an increasing risk of developing heart failure and automated evaluation of efficacy of therapy for patients with existing symptoms of heart failure. In a remote monitoring environment, the risk score enables monitoring of patients for early warning signs associated with an increased risk of heart failure or worsening symptoms of heart failure. Remote monitoring further enables automated, semi-automated, or manual monitoring of particular characteristics to evaluate efficacy of therapy for individuals within various stages heart failure. Real time monitoring can enable timely additional intervention or modifications to therapy as the disease state progresses. For example, real-time monitoring of therapy efficacy of individuals in early stage heart failure with elevated blood pressure on a specific medication, may potentially benefit from more aggressive medication regimen if and when the disease progresses.

Applied within an patient monitoring environment, the system enables monitoring of subjects or patients with high risk factors for developing heart failure. In many embodiments the patient monitoring environment is an ambulatory patient within a medical care facility such as a hospital or an outpatient clinic. Regardless of the type of facility, for patients the system can provide real time continuous monitoring of analytes and physical parameters that are indicative of the efficacy of ongoing therapy. Additionally, the real time continuous data can enable more frequent and responsive changes in therapy. For example, rather than having to wait for discrete ROS/ORP samples to be returned from a laboratory, with real time continuous monitoring physicians can easily see if ROS and/or ORP levels are increasing or decreasing and additionally the rate at which concentrations of the detected and measured analyte levels are changing. With rate of change data, physicians can change and modify treatment protocols and see the results of previous changes more rapidly than with discrete samples that may take hours to return from the laboratory.

In a remote monitoring environment, the system can further be transitioned from a medical care facility to a mobile monitor capable of operating as a home monitor or any other location outside of a medical care facility. Use of the system as a mobile monitor may be desirable for patients that may be considered high risk of developing heart failure, a later stage heart failure, or other diseases/conditions that can be detected via changes in the microcirculation.

The goal for remote monitoring is to provide early notification that a patient may be trending toward heart failure, or alternatively for patients already diagnosed with heart failure, the efficacy of therapy and treatment. In some embodiments of remote monitoring, notification is provided to the patient while in other embodiments the notification is provided to an attending physician. In still other embodiments, notification is provided to both the patient and at least one medical or care professionals such as, but not limited to an attending physician, nurse, resident healthcare provider, or a centralized care facility. Similar to patient monitoring use of the system as a remote monitor can result in a patient seeking more timely application of therapy.

Optionally enhancing each of the previously described modes for the system is interactive mode. Interactive mode is intended to prompt a user to perform specific physical actions or movements into order to obtain specific data in order to refine the risk score. Alternatively, the interactive mode can also be used to determine the effects of any treatment protocol and provide real-time, actionable information to external control algorithms whose aim is to optimize the management of therapy delivery. In many embodiments, this is accomplished by modifying therapy based on system outputs achieving targets and/or set points for specific risk metrics based on a specific clinical protocol.

FIG. 1 is an exemplary block diagram showing components within a system 100 to determine a risk score of developing heart failure, in accordance with embodiments of the invention. Broadly, the system 100 includes a sensor array 101 that includes analytes sensors 101a and physical sensors 101b powered by an electronics module 102 that further enables bidirectional communication with a plurality of remote devices, such as, but not limited to an external monitor 104, cloud computing systems 106 and mobile devices 128. The remote devices enable different aspects of functionality of the system 100, such as, but not limited to entry of patient specific data, display of historical and trending data acquired by the system 100, and machine learning. The totality of components shown in FIG. 1 enable the system 100 to be used across a variety of environments such as ambulatory patient monitoring and remote monitoring. However, embodiments tailored for a specific environment may not include all of the components shown in FIG. 1. For example, use of the system 100 as a remote monitor in a home may not utilize an external monitor 104. Likewise, when the system 100 is used as a patient monitor in a hospital environment, the system 100 may not include a mobile device 128. The inclusion of all of the components within FIG. 1 is intended to illustrate the flexibility and adaptability of the system 100 to be used in different environments. However, regardless of environment, an element of the system 100 that is required for all embodiments is the sensor array 101.

Sensor Array

Figure 2A:
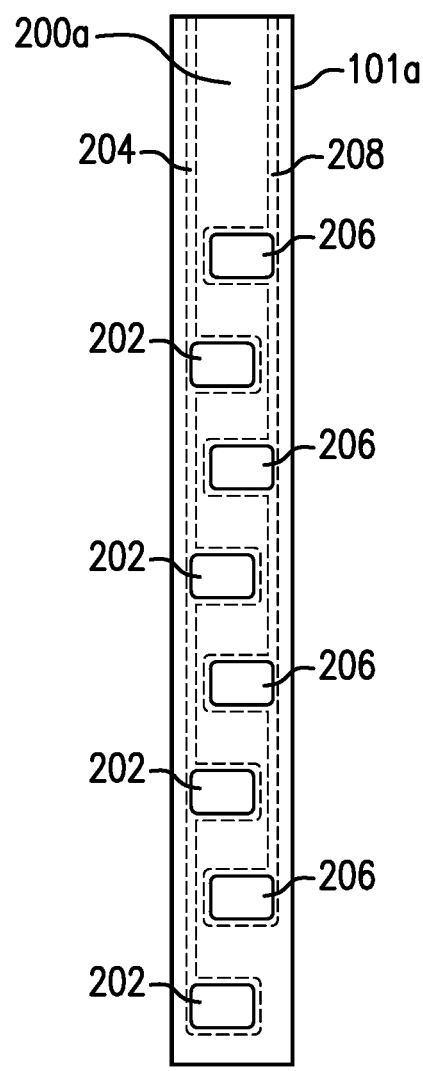
FIGS. 2A and 2B are exemplary views of an A-side and a B-side of a probe, or an analyte sensor, within the sensor array, in accordance with embodiments of the invention.
Figure 2B:
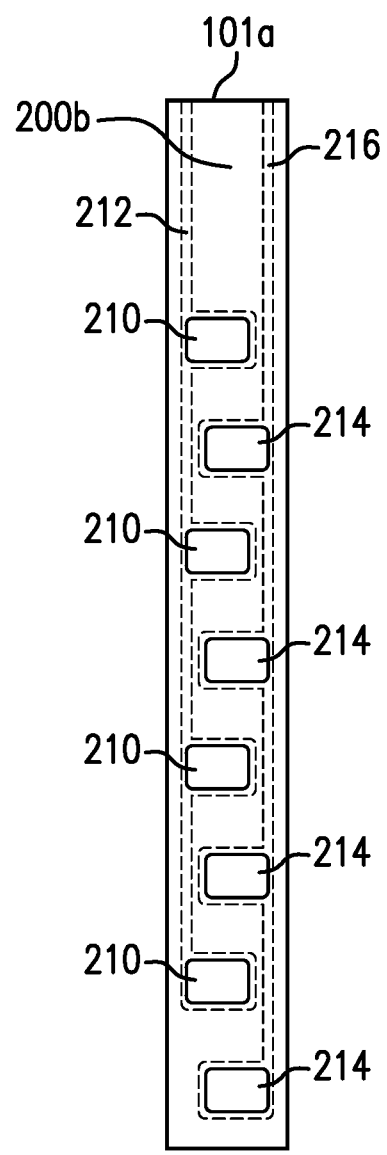

FIGS. 2A and 2B are exemplary views of an A-side 200a and a B-side 200b of an implantable probe, also referred to as an analyte sensor 101a, within the sensor array 101, in accordance with embodiments of the invention. In varying embodiments the sensor array 101 includes an analyte sensor having an A-side 200a and a B-side 200b that has the capability to continuously detect a single analyte or a plurality of analytes. While some embodiments of the analyte sensor 100a use both A-side and B-side, other embodiments utilize a single side. Exemplary analytes that can be measured on either A-side or B-side or both, include, but are not limited to glucose, lactate, oxygen, ROS, ORP or combinations thereof. Varying embodiments of the sensor array 101 include a single analyte sensor 101a or multiple analyte sensors 101a. In some embodiments the analyte sensor 101a, or implantable probe, can be implanted via a surgical procedure. In other embodiments, the analyte sensor 101a can be temporarily inserted into tissue, such as, but not limited to subcutaneous tissue, muscle tissue, organ tissue, or the like. In varying embodiments, the implantable probe may be temporarily inserted into tissue for varying durations that can be measured in minutes, hours, days, weeks, or months. While many embodiments of the implantable probe, or analyte sensor 101a have been discussed as using both an A-side 200a and B-side 200b, other embodiments utilize a single side of the implantable probe. In these embodiments the requisite sensor elements are found either on a single side of the implantable probe and distributed across other sensor features within the sensor array.

FIG. 2A is a view of the A-side 200a that includes electrode first electrode 202 and second electrode 206 along with corresponding first electrode trace 204 and second electrode trace 208. Depending on manufacturing techniques, the first and second electrodes can be transducers configured to measure an analyte or a combination counter/reference electrode or discrete counter electrode and reference electrode. FIG. 2B is a view of the B-side 200b that includes third electrode 210 and fourth electrode 216 along with corresponding third electrode trace 212 and fourth electrode trace 216. Similarly to the electrodes on A-side 200a, the third and fourth electrodes 210 and 214 can be configured to measure an analyte or as combinations of counter/reference electrodes. In embodiments where the sensor array 101 includes a single analyte sensor 101a configured to measure glucose and lactate.

In some embodiments the sensor array 101 includes a combination of oxygen, reactive oxygen species (ROS), redox potential (ORP), glucose, and/or lactate sensors. In other embodiments, the sensor array 101 includes at least one each of oxygen and ROS sensing transducers. In many embodiments, the respective sensors for oxygen, ROS, ORP, glucose, and lactate are electrochemical sensors that include multiple electrodes or transducers that are dispersed along and/or among A-side 200a and B-side 200b. For example, the oxygen sensor can include a single or multiple oxygen measuring electrodes found on either A-side or B-side 200a/200b. Implementation of multiple electrodes for a particular analyte can enable redundancy or may be necessary to generate sufficient measurable electrical current.

The sensor array 101 further includes additional sensors or abilities to measure physical characteristics such as, but not limited to movement (via accelerometers), temperature, tissue impedance (such as tissue hydration levels related to development of edema), skin impedance and sensor hydration levels. Measurement of some physical characteristics is enabled via physical sensors or other instrumentation incorporated within or on the electronics module. Additionally, in many embodiments, physical characteristics are determined via a combination of the analyte sensors 101a implanted within the subject and the physical sensors 101b associated with the electronics module. In one embodiment, physical characteristics are obtained via a skin contacting electrode located on an exterior surface of a sensor assembly, as will be discussed in more detail below. The specific physical sensors discussed should not be construed as limiting. Other and additional physical characteristics from physical sensors associated with the sensor array 101 can be used as risk metric inputs to the risk score. Monitoring hydration levels of at least one, some, or all of the sensors within the sensor array 101 enables detection of whether the sensor array 101 is properly implanted within desirable tissue. Additionally, monitoring the sensor elements for proper hydration can be used as a trigger to enable at least one of calculation of a risk score, data recording, and/or data transmission.

Electrochemical impedance spectroscopy applied across any electrode pair within the sensor array 101 can be used to measure or infer tissue impedance to determine tissue hydrations levels, or a fluid status within subcutaneous tissue of a subject being monitored. Congestive heart failure decreases the ability of the heart to pump blood throughout the body. In the aggregate, this can result in fluid build up in the periphery, particularly in the lower legs. Therefore, increased fluid build up may be a minor initial indicator or symptom of heart failure. Utilizing the sensor array enables continuous monitoring of tissue impedance to detect changes in fluid content within the interstitial space. In some embodiments an EIS scan is across specific frequencies is used to correlate impedance with sodium concentrations within tissue surrounding the sensor via either a lookup table or via an equivalent circuit model. Regardless of how impedance is determined, real-time monitoring can enable EIS measurements over time to determine if there is and increase in fluid within interstitial fluid based on changes in salinity of the interstitial fluid. If salinity decreases, one can infer there is additional fluid build up. Conversely, if salinity increases, it can be inferred that the fluid level within the interstitial fluid is decreasing. Increased, or increasing fluid within interstitial fluid results in lower relative impedance, measurable across multiple frequencies. Thus, as tissue impedance drops, the risk for edema is increased thus also resulting in an increased risk of developing heart failure as well. In some embodiments, fluid status of a subject is a risk metric contributing to the risk score of developing heart failure because fluid status provides context and a normalizing factor for other measurements, such as, but not limited to tissue oxygen levels and concentrations of ROS and ORP. Absolute and trend information derived from tissue hydration levels enable adjustment or modifications to a risk score In still other embodiments, tissue hydration levels enable additional insight regarding perfusion of analytes within different types of tissues. For example, in various embodiments tissue hydration levels for a sensor array 101 placed in muscle provides additional or less information than a sensor array 101 that is placed in adipose tissue.

In some embodiments data from a single analyte sensor is combined with data from any to all of the physical characteristic sensors to determine a risk score of developing heart failure. In other embodiments multiple analytes from either a single sensor or multiple analyte sensors is used in conjunction with the data from any one to all of the physical characteristic sensors to determine a risk score of developing heart failure. The rationale for enabling risk score calculations based on less than every data stream from the sensor array is to enable tailoring of the sensor array to a particular environment. For example, if a patient is breathing with assistance of a ventilator or receiving oxygen via an oxygen mask, it may not be preferred to have a risk score factor in data acquired via the tissue oxygen sensor, ROS and/or ORP. Alternatively, when using an ventilator or using an oxygen mask it may be advantageous to include tissue oxygen, ROS and/or ORP in order to determine efficacy of therapy via expected or predicted changes in the microcirculation.

In many embodiments, the analyte sensor 101a is intended to be placed in subcutaneous tissue where the plurality of working electrodes within the sensor array 101 produce signals related to the analyte each transduced is configured to measure or detect. In embodiments where the analyte sensor is intended to be placed within subcutaneous tissue, the analyte sensor 101a may also be referred to as a probe. Placement within subcutaneous tissue enables a unique perspective for an oxygen sensor that is substantially different than common SpO2 oxygen measurements. Specifically, with embodiments of the analyte sensors 101a, oxygen within tissue is being measured rather than a measurement of SpO2 that is an estimation of arterial oxygen. When determining a risk score of developing heart failure it is advantageous to measure oxygen within tissue rather than estimated arterial oxygen because oxygen within tissue is a direct measurement of oxygen perfusion.

Supplementing the tissue oxygen signal are signals from transducers configured to measure ROS and ORP. In some embodiments, a two-electrode system is employed where each of the working electrodes electrochemically measure a particular analyte relative to a counter electrode. In other embodiments, a three-electrode system is employed where each of the working electrodes electrochemically measure a particular analyte relative to a counter and reference electrode. In one embodiments, ROS and ORP would be enabled via pairs of electrodes. An ROS measurement can be acquired through a first pair of electrodes that includes a standard working electrode and a combined counter/reference electrode, also referred to as a pseudo-reference electrode. An ORP potential can be obtained via a potentiometric measurement between the pseudo-reference electrode and a standard reference electrode. In many embodiments the sensing or measurement electrodes can are collated on a first side of a probe while the pseudo-reference and standard reference electrode are formed on a second side of the probe.

In preferred embodiments the ROS and ORP sensors would provide calibration free, real-time concentration levels of oxidizing and antioxidant agents. Because it may be difficult to determine what a body is doing to combat oxidative stress ROS measurements alone may provide minimal insights to determination of a risk score. However, measuring the concentration of ROS along with ORP can provide a holistic perspective of both measurements. In many embodiments low ROS and low ORP would be indicative of a low risk scenario, while elevated ROS and elevated ORP would be indicative of highest risk. While the ROS and ORP measurements can be used as a component in determining a risk score, the measured ROS and ORP values can also be displayed as real-time discrete measurements for clinicians to monitor and consider when evaluating a patient.

In some embodiments, each working electrode has a corresponding counter electrode while in other embodiments multiple working electrodes share a counter electrode. In still other embodiments, two working electrodes share a counter electrode while the third working electrode has a dedicated discrete counter electrode. Furthermore, the various embodiments of working electrodes and counter electrodes can be distributed among separate and discrete substrates. Typically, working electrodes and counter/reference electrodes are formed on a single substrate. However, an electrode design intended for use in the invention allows the complete physical separation of any of the working electrodes and any of the counter/reference electrodes. For example, as is shown in FIGS. 2A and 2B working electrodes for analyte sensors can be formed on A-side 200a while counter/reference electrodes are formed on B-side 200b. While the various electrodes may be separated on distinct A-side and B-side, in many embodiments the sensor array 101 having the plurality of working electrodes is inserted into the subcutaneous tissue via a single point of insertion. The use of a single insertion point minimizes both patient discomfort associated with insertion and insertion complexity.

Figure 2C:
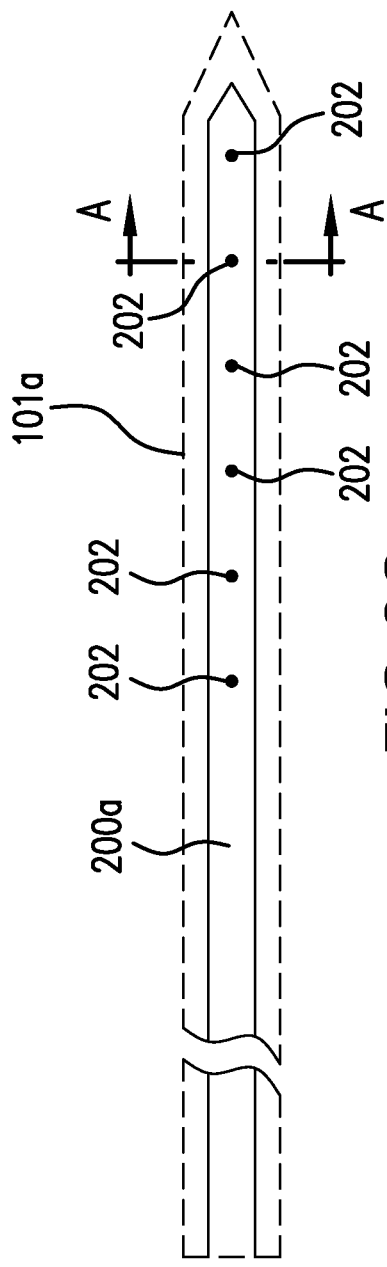
FIG. 2C is an exemplary top view of an analyte sensor in accordance with various embodiments of the present invention.

FIG. 2C is an exemplary top view of a analyte sensor 200a in accordance with various embodiments of the present invention. The analyte sensor 200a in FIG. 2C is intended to be an exemplary single analyte sensor having first electrodes 202 distributed across the sensor. In particular embodiments, the analyte sensor 200a in FIG. 2C is an exemplary oxygen sensor capable of measuring oxygen within the tissue into which it is inserted. In many embodiments the preferred tissue is subcutaneous tissue, however this should not preclude the use of the sensor in other tissues such as, but not limited to skeletal muscle tissue, smooth muscle tissue or even organ tissue. Insertion of an oxygen sensor into any of these types of tissues can provide insight into the microcirculation of the specific tissue, and accordingly, the relative health of the subject.

Figure 2D:
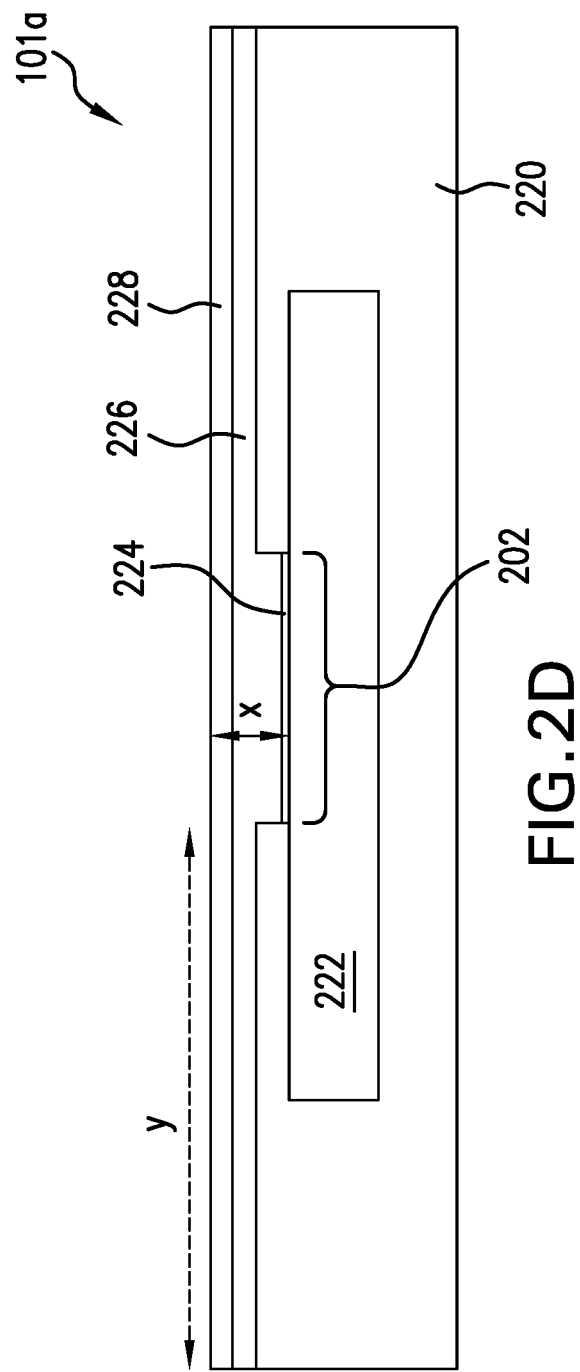
FIG. 2D is an exemplary view of cross-section A-A of the analyte sensor in FIG. 2C, in accordance with embodiments of the present invention.

FIG. 2D is an exemplary view of cross-section A-A of the analyte sensor 101a in FIG. 2C, in accordance with embodiments of the present invention. The simplified cross-section includes a conductor 222 that is surrounded by insulation 220. An opening in the insulation 220 exposes a recessed portion of the conductor 222 thereby enabling the formation of the first electrode 202. In some embodiments the exposed conductor 222 is processed to create electrode surface 224. The electrode surface 224 in many embodiments is based on a platinum material that is electroplated onto the exposed conductor. Covering the platinum electrode is a hydrogel 226 that is itself covered in material 228 that is preferably selected from either hydrophobic or oxygen permeable materials. A hydrophobic or oxygen permeable membrane placed over the hydrogel 226 without sealing the hydrogel 226 from the surrounding tissue or vasculature can preferentially passes oxygen over other chemistries present in the tissue or vasculature surrounding the sensor such that primary transport direction for oxygen is normal to the direction of electrolyte transport.

Use of silicone based materials for material 228 can generally fulfill both requirements as many silicone based materials are both hydrophobic and oxygen permeable. This can result in a patterned multi-layer polymeric hydrogel that extends normally (dimensionally identified as "x" in FIG. 2D) and laterally (dimensionally identified as "y" in FIG. 2D) from the platinum electrodes where the normal distance "x" is significantly smaller than the lateral distance "y". Having the ratio between normal distance and lateral distance provides transport resistance to the underlying platinum sensing electrode thereby restricting consumption of oxygen that helps prevent depletion in the tissue or vasculature adjacent to the implanted sensor. Additionally, the ratio between normal distance and lateral distance further provides an electrolyte or conductive pathway for ionic transport from the platinum electrode to the surrounding tissue or vasculature and then to an auxiliary or counter electrode located elsewhere on the probe.

Though not illustrated, in preferred embodiments of the overall electrochemical sensor design includes a combined counter and reference electrode, commonly referred to as a pseudo-reference electrode. The pseudo-reference electrode completes the electrochemical surface and is preferably located on a surface different, or even opposite to the surface containing the first electrodes 202. For example, using the embodiments shown in FIGS. 2A-2B, the working electrodes 202 are formed on side-A 200a while the pseudo-reference electrode or electrodes are formed on side-B, 200b.

Figure 2E:
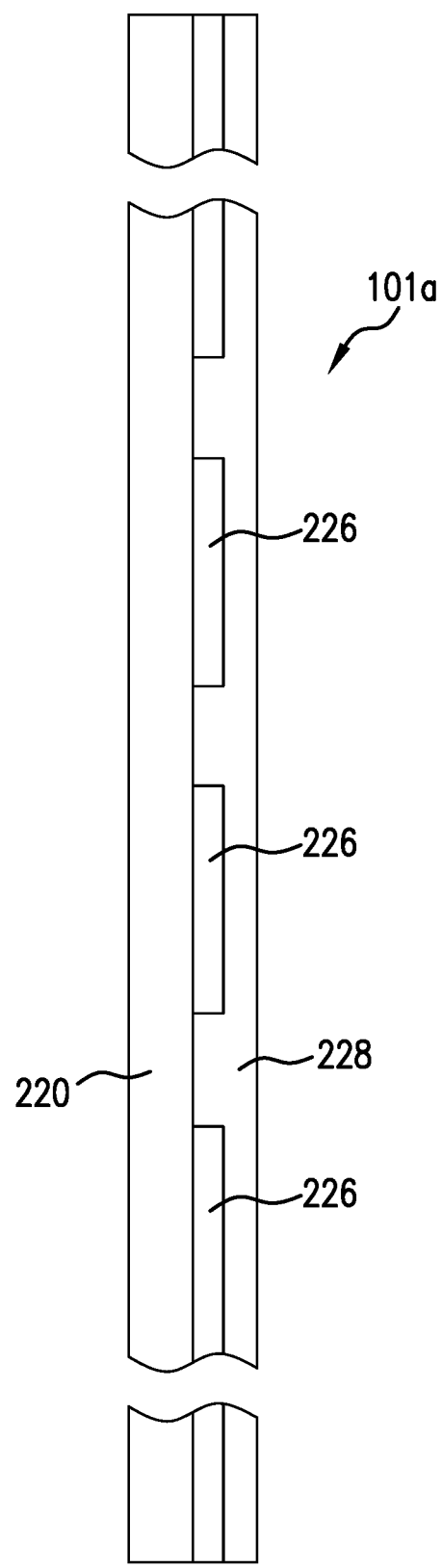
FIG. 2E is an exemplary side view of a sensor assembly that includes patterned hydrogel, in accordance with embodiments of the present invention.

FIG. 2E is an exemplary side view of a sensor assembly 101a that includes patterned hydrogel 226, in accordance with embodiments of the present invention. In this embodiment, hydrogel 226 is selectively applied over individual electrodes. As the illustration in FIG. 2E is a exemplary side view, the hydrogel 226 is applied to the edge of the sensor assembly and material 228 is applied over the hydrogel 226. Note that material 228 does not completely envelope the hydrogel 226 as the hydrogel 226 is exposed along the edge of the sensor assembly.

The hydrogel 226 is processed in a manner that allows both a variable number of layers of a single or multiple hydrogels to be placed over each exposed electrode elements in order to provide preferential pathways for electrolyte and chemical transport. The embodiments shown in FIG. 2E enables a discontinuity in the electrolyte at select portion of the interface between the implanted electrochemical sensor and the tissue or vasculature to allow exchange of molecules that support the mechanical integrity of the sensor and allows the fresh supply of reactants and electrolyte components to support a stable environment for the electrochemical sensor and to maintain the half cell potential and environment for the reference electrode or combined counter reference electrode.

The specific single analyte embodiments discussed in FIGS. 2C-2E should not be construed as limiting. Additionally, while use of the single analyte embodiments in FIGS. 2C-2E was confined to detecting tissue oxygen, one skilled in the art should recognize the ability of electrochemical sensors to measure a plethora of different analytes based on changes to at least chemistry, structure or both. Furthermore, the various other embodiments described above should not be construed as limiting. For example, while the embodiments above have the sensors being distributed along the length of the sensor, other embodiments have have sensors in a continuous or contiguous configuration. Alternatively, an A-side may have distributed sensor elements while a B-side may include continuous, contiguous or even distributed sensor elements. The sensor array should not be perceived as limited to subcutaneous placement. Nor should the sensor array be construed as being limited to measurements of oxygen and ROS. In many embodiments, the various electrodes on a single analyte sensor can be used to measure impedance across multiple frequencies within the tissue. Additionally, in some embodiments the various electrodes can enable acquisition of ECG measurements. In embodiments configured to measure impedance and ECG, sampling of each measurement can occur periodically at staggered intervals to avoid interfering with the other measurements. In other embodiments additional sensing electrodes can be formed on the sensor that measure analytes such as, but not limited to, glucose and lactate. In order to accommodate additional analyte sensing electrodes it may be necessary for some analytes to share a common reference electrode. Alternatively, some embodiments use more than a single analyte sensor 101a. In embodiments where multiple analyte sensors 101a are utilized, redundant electrodes for measuring different analytes can be formed on each, or both analyte sensor. Alternatively, a first analyte sensor may include a plurality of working electrodes while a second analyte sensor may include a shared, or a plurality of counter and/or reference electrodes. Other embodiments, for use in diagnosing or determining risk scores for other conditions or diseases can employ various sensors to measure other combinations of analytes in different locations within the subject.

Electronics Module

Returning to FIG. 1, the system 100 additionally includes an electronics module 102 that provides power for the sensor array 101 and enables bidirectional communication with other system components such as, but not limited to the external monitor 104, cloud computing systems 106 or mobile devices 128. Enabling the electronics module 102 to perform such tasks are electronic module components such as, but not limited to a communication module 108, a processor 110, memory 112, and a power supply 114 enclosed within an electronics module case. The electronics module 102 includes additional components, however, the specific components found in FIG. 1 warrant discussion regarding operation of the system 100.

In preferred embodiments the power supply 114 provides power to the electronics module 102 and also to the sensor array 101. Batteries, rechargeable or disposable, can be used for the power supply 114. In order to minimize the likelihood of fluid ingress to the electronics module, it may be preferable to use inductive charging for embodiments using rechargeable batteries. Other embodiments use alternatives to batteries such as, but not limited to capacitors, supercapacitors, solar cells, fuel cells and the like. The specific examples provided for the power supply 114 should not be construed as limiting. Rather, the examples provided should be viewed as examples of portable power supplies capable of supplying the electronics module 102 and the sensor array 101 with power for the expected life of the system 100.

In some embodiments the processor 110 is custom circuit such as but not limited to an application-specific integrated circuit (ASIC) or field programmable gate array (FPGA). In other embodiments the processor 110 is a more generic system on chip (SoC) or system in package (SiP). In instances where a SoC or SiP is utilized, communication module 108 and memory 112 can be integrated within the SoC or SiP. In many embodiments the processor is in communication with the sensor array 101 receiving raw signal data from the plurality of working electrodes and other sensors. In some embodiments the processor 110 performs minimal manipulation of the raw data from the working electrodes. Examples of minimal manipulation include, but are not limited to filtering noise and compression. In these embodiments the data from the working electrodes is transmitted to a multitude of external devices via the communication module 108 where processing is completed to produce a risk score for heart failure. Alternatively, in other embodiments the processor 110 executes stored instructions to process the sensor data before transmitting processed data that may include a risk score for heart failure to any external devices via the communications module 108.

In many embodiments the electronics module 102 is coupled to the sensor array 101 during an insertion process. In most embodiments the electronics module 102 includes a housing that when coupled with the sensor array, seals the combined sensor array 101 and electronics module 102 within a housing that defines an on-body assembly 300.

Figure 3A:
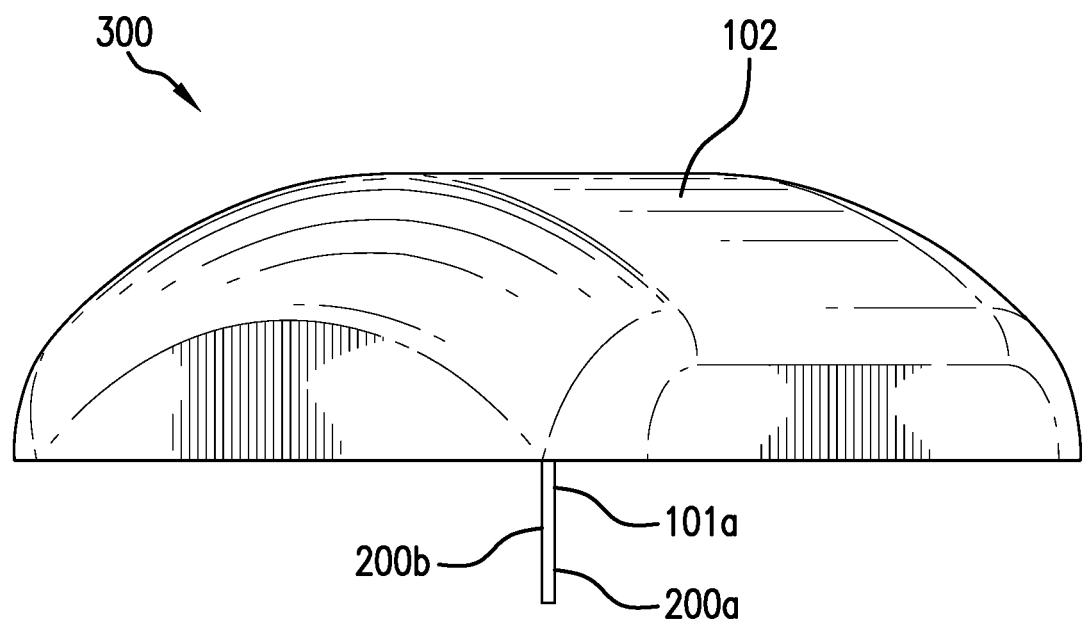
FIGS. 3A and 3B are exemplary views of different on-body assemblies, in accordance with various embodiments of the present invention.
Figure 3B:
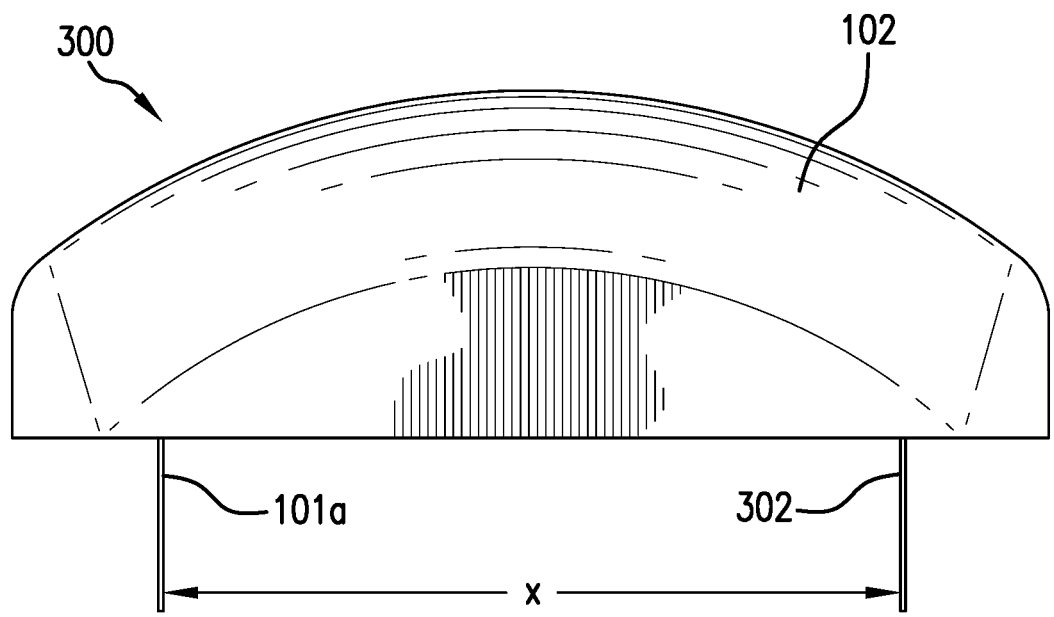

FIGS. 3A and 3B are exemplary views of different on-body assemblies 300, in accordance with various embodiments of the present invention. In FIG. 3A the on-body assembly 300 is illustrated with the analyte sensor 101a having been deployed from the electronics module 102. FIG. 3B is an exemplary side-view illustration of an embodiment of a sensor assembly 300 that includes a first analyte sensor 101a and the second analyte sensor 302. Both the first and second analyte sensors 101a/302 are shown extended from the electronics module 102. Furthermore, a distance X separates the first analyte sensor 101a from the second analyte sensor 302. One benefit of having multiple analyte sensors is the potential to detect and measure and robust ECG measurement between the first and second analyte sensors 101a/302. Distance X between the first and second analyte sensors 101a/302 can improve the ability to produce a robust ECG signal that otherwise may be difficult to obtain on a single minimally invasive analyte sensor.

In the embodiment illustrated in FIG. 3B electrodes for the ROS, ORP and oxygen sensors may be distributed or combined onto the first analyte sensor 101a and the second analyte sensor 302. For example, in one embodiment the first analyte sensor 101a contains all the elements needed for the ROS and ORP sensor while the second analyte sensor 302 combines all the elements for the oxygen sensor. In another embodiment, half of the electrode for the ROS and ORP sensors are positioned on the first analyte sensor 101a while the second half or the electrodes are on the second analyte sensor 302. Likewise, the working electrode of the oxygen sensor is positioned on the second analyte sensor 302 and the reference electrode, or pseudo-reference electrode, is positioned on the first analyte sensor 101a. One potential advantage of distributing both working and reference/pseudo-reference electrodes for both ROS and oxygen onto the first analyte sensor 101a and the second analyte sensor 302 is having redundant measurements from analyte sensors in different locations. If different data is acquired from the first analyte sensor 101a and the second analyte sensor 302, the electronics within the sensor housing can perform diagnostic testing on either or all of the sensors to determine how to best to resolve any difference in sensor readings. Exemplary diagnostics include, but are not limited to changes in potential, changes in offset voltages/currents, and pre-programmed electrochemical impedance spectroscopy tests. The results of the tests on the first and second analyte sensors 101a/302 can result in corrections being automatically applied to one or both sensors such as taking weighted average between sensor values from the different sensors. Additionally, signal integrity checks can be used to determine weighting between sensors. Alternatively, weight values from one or more sensors can be applied if there are signal integrity problems In embodiments using multiple analyte sensors each analyte sensor can be inserted to identical depth or to different depths. For example, the first analyte sensor 101a may be inserted into subcutaneous tissue while the second analyte sensor 302 is inserted into the dermis. In some embodiments where each analyte sensor is inserted to a substantially same depth, electrode placement on the analyte sensor itself can accomplish measuring analytes at different insertion depths. For example oxygen sensing electrodes can be located toward the distal end of the first analyte sensor and closer to the proximal end of the second analyte sensor. By having electrodes and/or sensors at different depths within a subject a better understanding of the microcirculation within the subject can be acquired. Another benefit of electrodes and sensors at different depths is the increased path length when measuring impedance between electrodes on different analyte sensors and ECG.

In various embodiments utilizing a first and second analyte sensor, impedance measurements may be made with the first analyte sensor 101a, the second analyte sensor 302, or a combination thereof using alternating current or direct current or a combination thereof. When impedance measurements are made between electrodes on a single analyte sensor, the measurement is considered an intraprobe impedance measurement. When impedance measurements are made between an electrode on the first analyte sensor and an electrode on the second analyte sensor, the measurement is considered an interprobe measurement. Interprobe measurements can be measured at various combinations of depths. For example between an electrode at the distal end of each probe, or between an electrode at the distal end of the first analyte sensor and an electrode closer to the skin on the second analyte sensor. The ability to get a picture of impedance through various layers can enable actionable data regarding the presence or development of edema. Because edema measurements may vary depending on the location of the device/sensors, it may be necessary to record the physical location of the device on a subject. Recordation/entry of the physical location can enable data to be corrected or calibrated to more accurately reflect an overall status of a subject.

Figure 4A:
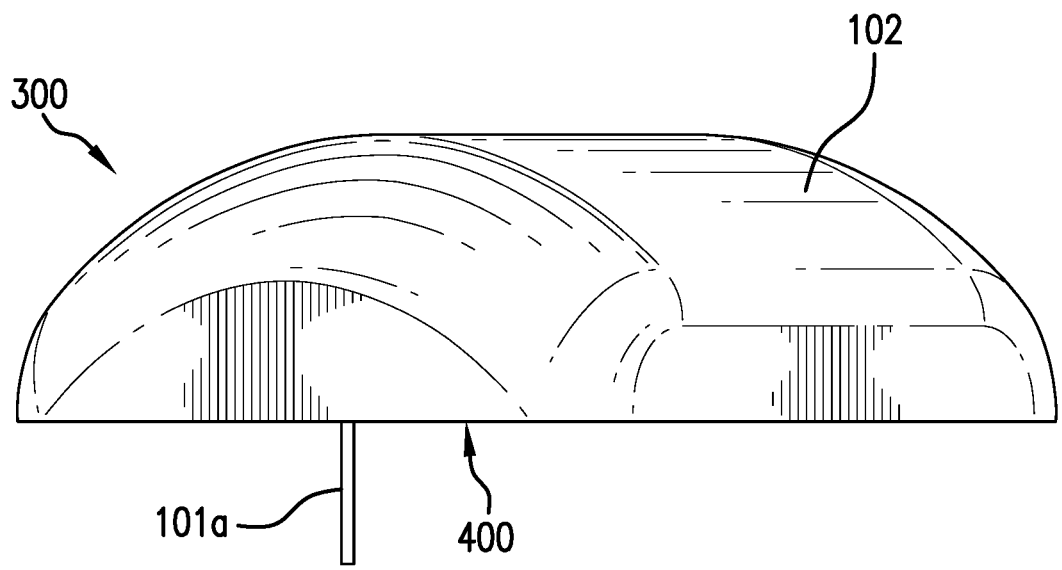
FIGS. 4A and 4B are exemplary pseudo-isometric illustrations of a sensor assembly having a first analyte sensor extending away from a skin contacting surface that includes a skin contacting electrode, in accordance with embodiments of the present invention.
Figure 4B:
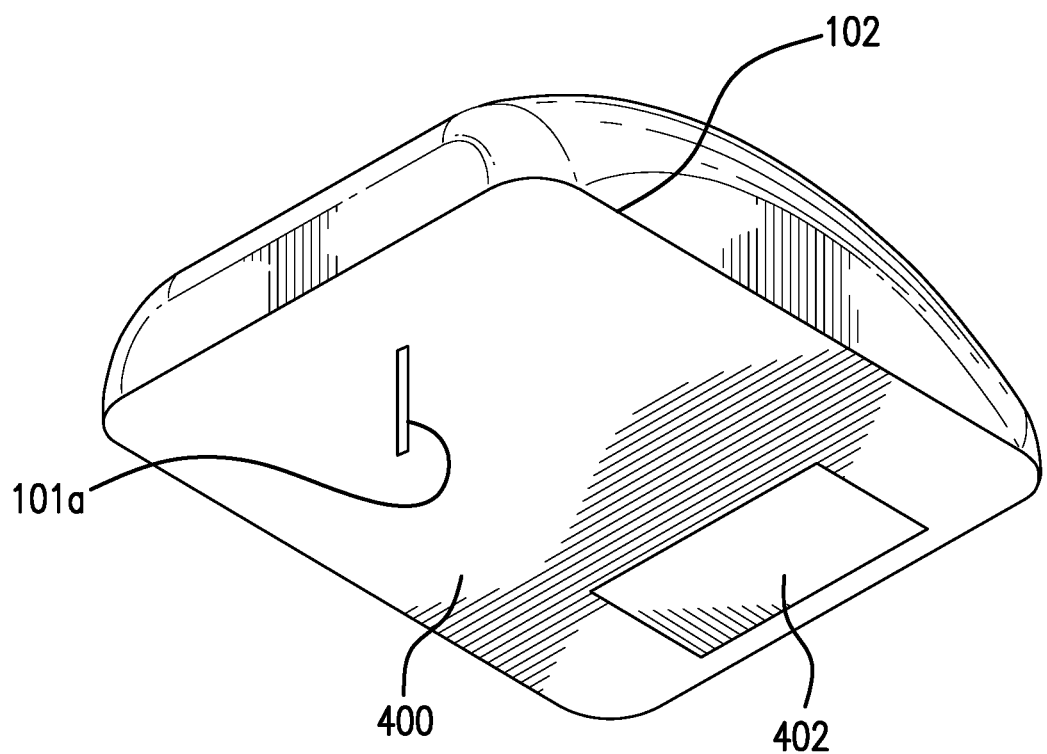

FIGS. 4A and 4B are exemplary pseudo-isometric illustrations of a sensor assembly 300 having a first analyte sensor 101a extending away from a skin contacting surface 400 that includes a skin contacting electrode 402, in accordance with embodiments of the present invention. Both FIGS. 4A and 4B show sensor assembly 300 with the analyte sensor 101a extending away from a bottom surface of the sensor assembly 300 to an exemplary insertion depth. FIG. 4B shows skin contacting electrode 402 located on the bottom of the sensor assembly 300 that is not visible in the view shown in FIG. 4A. The skin contacting electrode 402 is used in conjunction with the electrodes on the analyte sensor 101a to detect ECG signals and/or impedance. Similar to having the second analyte sensor from FIG. 3B, the skin contacting electrode 402 creates a larger separation distance between electrodes used to measure or detect ECG signals. Locating the skin contacting electrode 402 on the bottom surface of the sensor assembly 300 enables continuous measurements to be taken between the analyte sensor 101a and the skin contacting electrode 402. Alternatively, measurements between the analyte sensor 101a and the skin contacting electrode 402 can be taken at regular intervals that can vary dynamically between partial and whole seconds, minutes and hours.

Typically, the skin contacting surface 400 includes adhesive to secure the sensor assembly 300 in place on the skin for at least an expected wear-time that can vary between hours and multiple days. Embodiments having the skin contacting electrode 402 can include a flexible, conductive adhesive that cooperatively assists in retaining the sensor assembly 300 on the subject for the expected wear-time.

Figure 5A:
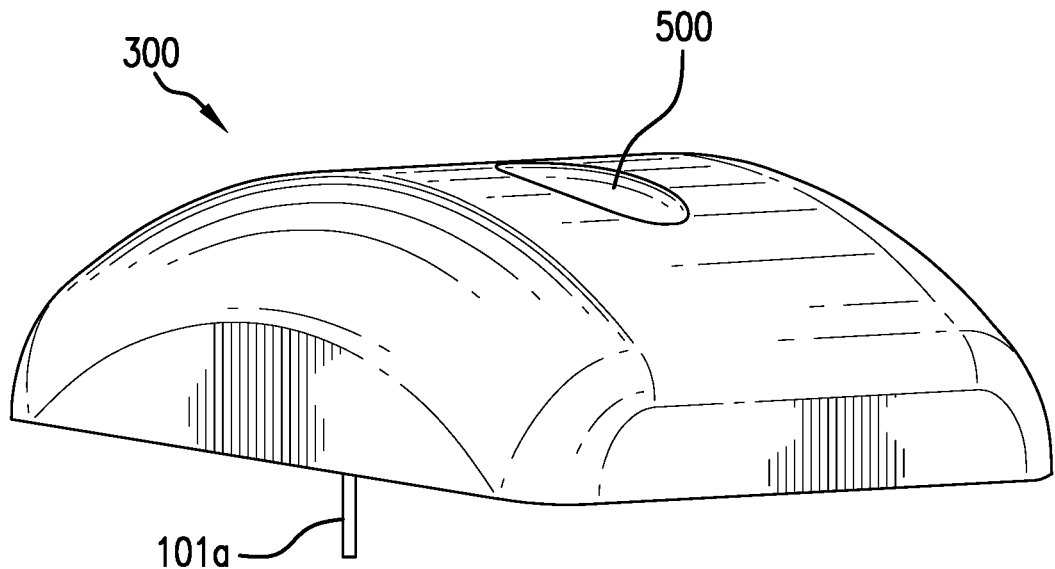
FIG. 5A is an exemplary isometric view of a sensor assembly that includes an implantable analyte sensor and and exterior facing electrode, in accordance with embodiments of the present invention.

FIG. 5A is an exemplary isometric view of a sensor assembly 300 that includes an implantable analyte sensor 101a and and exterior facing electrode 500, in accordance with embodiments of the present invention. Rather than contacting the skin surface when the sensor assembly 300 is attached to the subject, the exterior facing electrode 500 is configured to use a thumb or finger to obtain a discrete ECG measurement between the exterior facing electrode 500 and the analyte sensor 101a. Because using the exterior facing electrode 500 results in substantially more discrete rather than continuous data users may be prompted to acquire a discrete measurement or have a measurement taken whenever skin contact with the exterior facing electrode 500 meets a threshold value for taking a measurement.

One benefit of measuring an ECG between the exterior facing electrode 500 as a second electrode in conjunction with the analyte sensor 101a as the first electrode is the ability to use an opposite hand or limb to be used on the second electrode. The additional distance between the analyte sensor 101a and the limb/appendage/digit that contacts the second electrode may help optimize the ECG signal. The resulting discrete ECG measurements, with potentially optimized ECG signal, may be preferred for verification, confirmation or validation of a specific condition or state but continuous ECG data may be preferred for determination of a risk score.

Figure 5B:
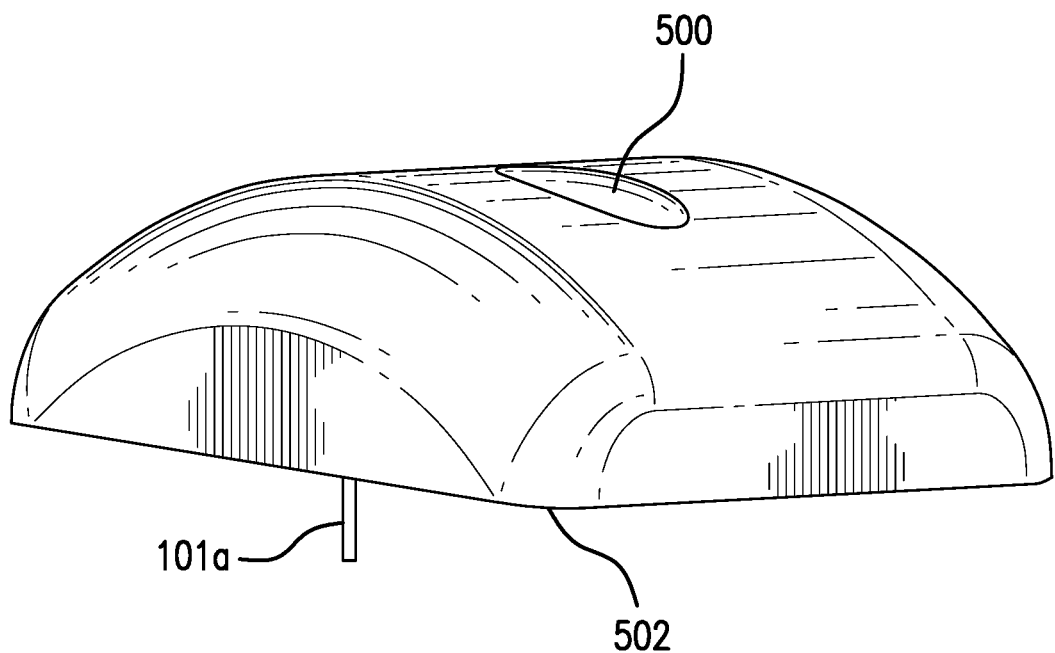
FIG. 5B is an exemplary isometric view of a sensor assembly that includes an implantable analyte sensor, and exterior facing electrode and skin contacting electrode in accordance with embodiments of the present invention.

FIG. 5B is an exemplary isometric view of a sensor assembly 300 that includes an implantable analyte sensor 101a, an exterior facing electrode 400 and skin contacting electrode 502 (not shown, but as described in FIG. 4B), in accordance with embodiments of the present invention. The embodiment shown in FIG. 5B is intended to include the skin contacting electrode discussed in FIG. 4B with the sensor assembly 300 from FIG. 5A. The combination of the analyte sensor 101a, skin contacting electrode 502 and exterior facing electrode 502 enables ECG measurements between each of the various electrodes. For example, continuous ECG data can be acquired between electrodes incorporated on the analyte sensor 101a and the skin contacting electrode 502. Discrete ECG data can be obtained between the exterior facing electrode 500 and either or both of the electrodes on the analyte sensor 101a or the skin contacting electrode 502. Accordingly, configurations like those in FIG. 5C can be suited for both determination of a risk score and verification, confirmation or validation of a specific condition.

In FIGS. 5A and 5B the exterior facing electrode 500 is located on an exterior facing surface of the sensor assembly 300. In various other embodiments, the exterior facing electrode can be integrated onto or into a third party device, such as, but not limited to a mobile phone, smart watch or other body worn device. Alternatively, rather than using third party integration of the exterior facing electrode, a separate exterior facing electrode that is intended to be integrated with the system can be used to compliment or verify data.

Figure 5C:
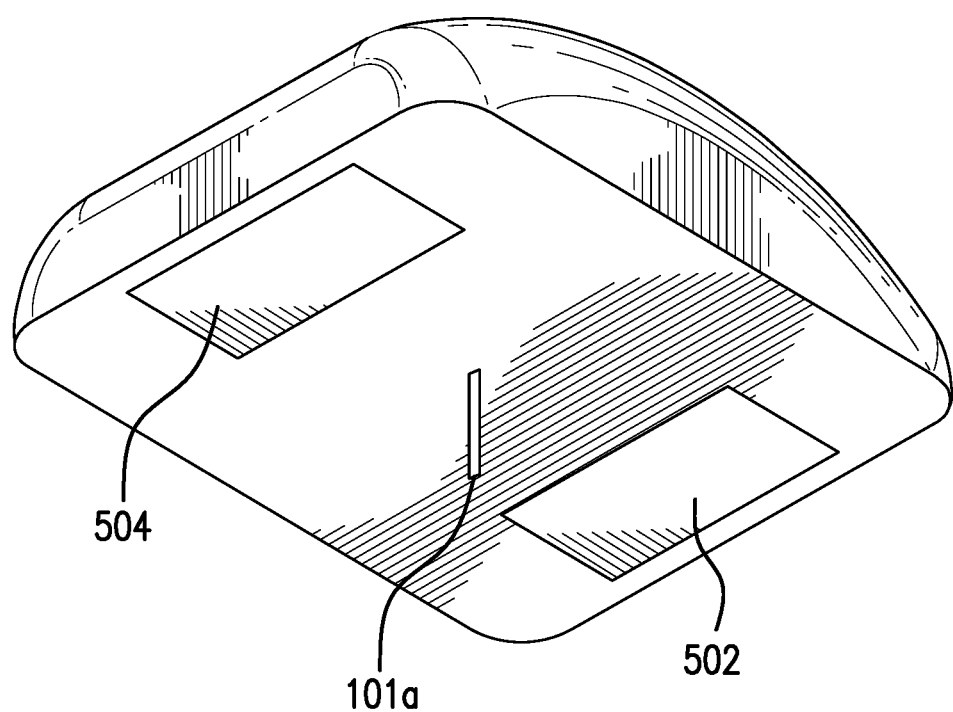
FIG. 5C is an exemplary pseudo-isometric view of a sensor assembly having an analyte sensor that is implantable, along with a first skin contacting electrode and a second skin contacting electrode, in accordance with embodiments of the present invention.

FIG. 5C is an exemplary pseudo-isometric view of a sensor assembly 300 having an analyte sensor 101a that is implantable, along with a first skin contacting electrode 502 and a second skin contacting electrode 504, in accordance with embodiments of the present invention. In embodiments incorporating a first skin contacting electrode 502 and a second skin contacting electrode 504, the use of the analyte sensor 101a in measuring or detecting ECG signals may be optional. For example, ECG signals can be measured continuously between the first skin contacting electrode 502 and the second skin contacting electrode 504. In embodiments where electrodes associated with the analyte sensor 101a are used to detect ECG signals, measurements between the analyte sensor 101a and either the first or second skin contacting electrodes 502/504 can contribute to ECG sensing. Alternatively, ECG signals determined using the analyte sensor 101a can be redundantly sampled or used to verify signals detected between the first and second skin contacting electrodes 502/504.

Figure 6A:
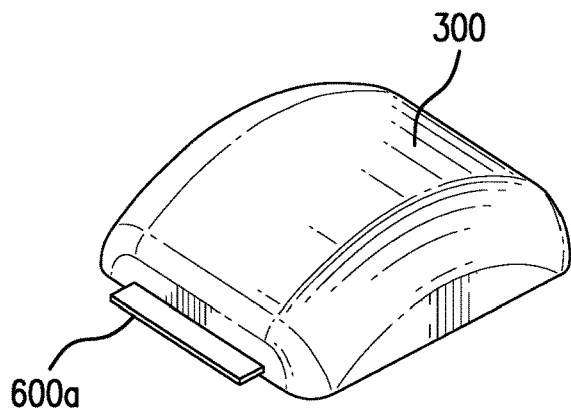
FIGS. 6A-6D are exemplary illustrations of a sensor embodiment having adjustable skin contacting leads, in accordance with embodiments of the present invention.
Figure 6B:
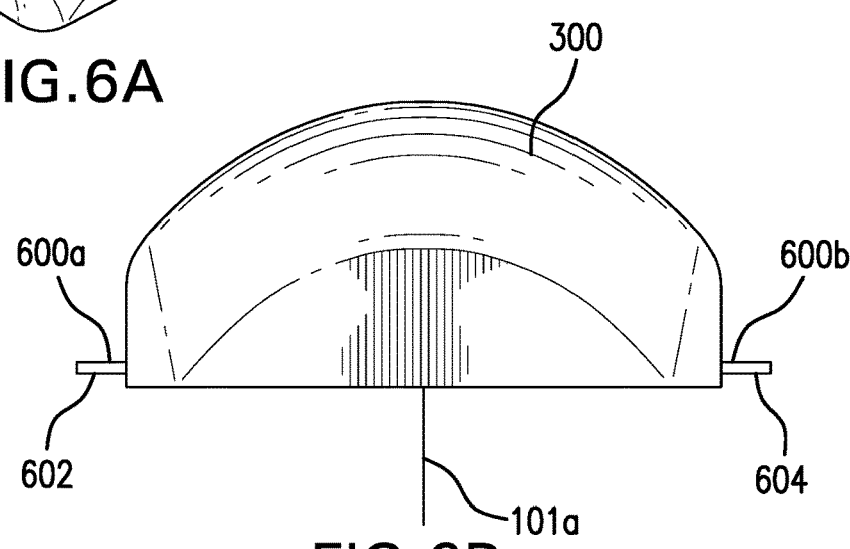

FIGS. 6A-6D are exemplary illustrations of a sensor embodiment 300 having adjustable skin contacting leads 600a and 600b, in accordance with embodiments of the present invention. In an effort to increase the distance between the skin contacting leads while maintaining or minimizing the footprint of the sensor assembly 300, the first skin contacting electrode can be located on a positionable lead 600a. While FIG. 6B shows the first and second skin contacting electrodes 602/604 associated with positionable leads 600a/600b, some embodiments may includes include first skin contacting electrode on a positionable lead while having a second skin contacting electrode formed on the skin contacting surface 400 (as shown in FIG. 4A). As described above in the discussion of FIG. 5C, ECG signals between either of the first or second skin contacting electrodes and the analyte sensor 101a can be optionally utilized to measure ECG signals.

Figure 6C:
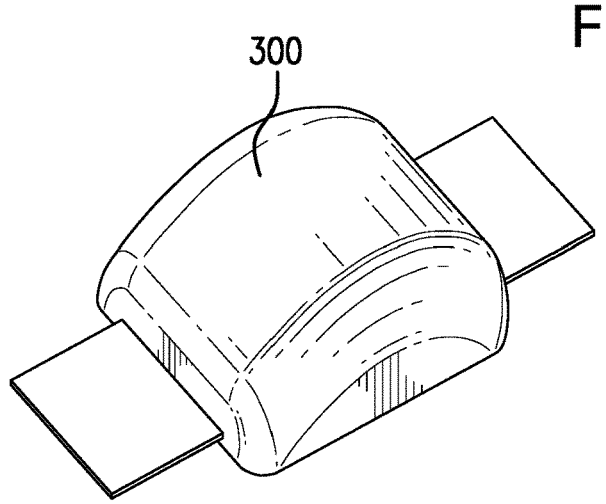
Figure 6D:
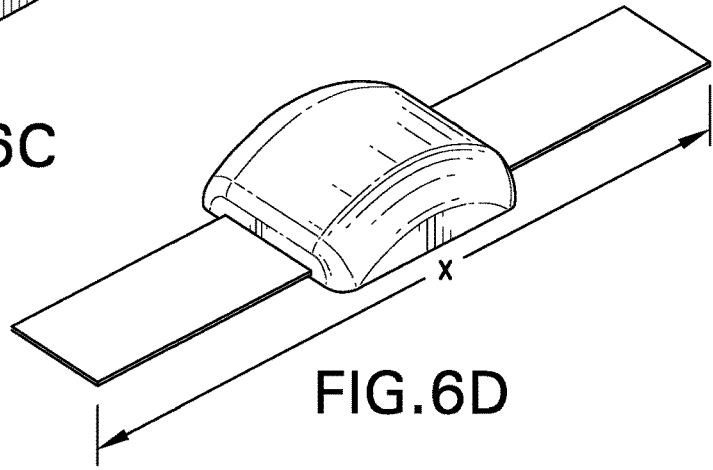

FIGS. 6C and 6D illustrate differences between a first position and a second position for the positionable leads 600a/600b, in accordance with embodiments of the present invention. In these embodiments in the first position (FIG. 6C) most of the positionable leads 600a/600b are intended to be retracted or contained within the sensor assembly 300. Deployment of the positionable leads 600a/600b to a second position (FIG. 6D) results in the the first and second skin contacting electrodes being separated by a distance X. In some embodiments the skin contacting electrodes are intended to be temporarily attached in the second position and after taking an ECG reading, the positionable electrodes and associated skin contacting electrodes can be returned to the first position. In other embodiments, the positionable leads are not intended to be retracted after deployment into the second position.

In FIGS. 6C and 6D, positionable leads 600*a* and 600*b* are exemplary illustrated as bands or tapes but in other embodiments, the positionable leads can also be comprised of flexible wires that further enhance the ability of the positionable leads to move more freely in various directions. Additionally, while FIGS. 6C and 6D show both positionable leads 600*a* and 600*b* both moving to the second position, some embodiments may include a single positionable lead and a skin contacting electrode may be incorporated on the skin contacting surface of the sensor assembly 300.

The various embodiments of the sensor assembly illustrated in FIGS. 3A through 6D should be construed as exemplary and various combinations of features described in each of the various embodiments can be combined into different embodiments. For example, the multiple analyte sensors disclosed in 3B can be applied to embodiments having a single or multiple skin contacting electrodes, positionable electrodes, and exterior facing electrodes. Similarly, a single sensor assembly may include multiple exterior facing electrodes that enables ECG signals to be detected between fingers on a right hand and a left hand.

Communications and Interconnectivity

In many embodiments the communications module 108 is based on personal area network technology commonly referred to as Bluetooth low energy (BLE) or Bluetooth Smart. In other embodiments, a customized or semi-custom communication standard is utilized. However, one common trait for any communication module 108 is the ability to securely send and receive data between at least a third party device and the electronics communication module 102. The ability to securely transmit either raw or processed data using the communications module 102 enables flexibility that allows the system 100 to be adaptable from a mobile monitor to being an integral component within a hospital ward.

In one embodiment data from the sensor array 101 is sent via the communications module 108 to a cloud computing system 106, also commonly referred to as "the cloud". In still other embodiments data from the sensor array 101 is transmitted via the communications module 108 to an external monitor 104. Clinical settings such as a hospital ward where multiple monitors display a plurality of condition being monitored for a patient could be ideal settings for embodiments where the electronics module 102 transmits to an external monitor 104 or the cloud 106. For example, with the appropriate infrastructure data from the sensor array 101 can be transmitted in real-time to an electronic medical record stored in the cloud 106. Alternatively, in some embodiments data can be transmitted from the external monitor 104 to the cloud 106 where it is stored as part of an electronic medical record.

In still other embodiments, the electronics module 102 transmits data from the sensor array 101 to a mobile device 128 such as, but not limited to a smartphone, a smartwatch, a portable fitness monitor, a tablet, a notebook computer, an ultrabook computer, or an aftermarket or integrated infotainment center for a vehicle. The examples of a mobile device 128 are not intended to be construed as limiting. Rather, the examples are intended to provide guidance regarding the types of devices that can receive and/or transmit data to the electronics module 102. Accordingly, devices that can be viewed as similar to those listed should be considered contemplated by the current disclosure. In embodiments where the mobile device 128 includes a connection to the internet, the mobile device 128 can send data to the cloud 106 where the data can be archived, shared with other devices, be further processed or become data to enable machine learning. Utilizing the data to enable machine learning further enables data-driven improvements such as development of algorithms that are patient specific or algorithms that are applied universally across all patients. For example, depending on how much information is provided with the data provided for machine learning, patient specific algorithms can include, but are not limited to factors such as age, race, weight, and pre-existing conditions. Similarly, regardless of patient specific information, all data processed via machine learning can be utilized to improve algorithms with the goal being improved outcomes for all patients.

Even with embodiments where additional processing is handled on either an external monitor 104 or the cloud 106, memory 112 can be used to store data from the sensor array 101 on the electronics module 102. Using the memory 112 to store data from the sensor array 101 can ensure sensor data is not lost if there are connectivity interruptions between the electronics module 102 and the external monitor 104, the cloud 106, or a mobile device 128. The memory 112 can further be used to store program instructions for the processor, or to store values for variables used by the processor 110 to output a risk factor for heart failure.

In many embodiments the electronics module 102 is removably coupled with the sensor array 101. With these embodiments, the electronics module 102 is capable of being reused after the sensor array 101 is deemed consumed or depleted. In other embodiments, a permanent coupling is achieved after an initial coupling between the electronic module 102 and the sensor array 101. In these embodiments, the electronics module 102 is considered disposable and is intended to be discarded after the sensor array 101 is deemed consumed. Alternatively, to reduce environmental impact, select portions of the electronics module, such as, but not limited to the power supply 114 and communications module 108 are recyclable. In many embodiments, initially coupling the electronics module 102 to the sensor array 101 provides power to the electrodes and initiates the program instructions stored in either the processor 110 or the memory 112.

In many of these embodiments, the electronics module includes a feedback device 113. The feedback device 113 provides feedback regarding the status of the combined electronics module 102 and sensor array 101. For example, in some embodiments the feedback device 113 is a single or a plurality of multi colored LED that blinks a first color and/or first pattern when the system is functioning with design parameters and a second color and/or second pattern if there is an error within the system. In other embodiments, the LED is a single color that uses different frequency of blinks to convey status of the system. In still other embodiments, the feedback module includes a vibration device similar those used in mobile phones to convey status of the system. In still other embodiments, a piezo or other audible sound emitting device is used as the feedback device 113.

The external monitor 104 may include some components not found in the electronics module 102, such as a graphic user interface (GUI) 122 and a display 124. Other components of the external monitor 104, such as a communication module 116, a processor 118, a memory 120 and a power supply 126 may seem duplicative of components in the electronics module 102, but may have different or improved capabilities or functionality. For example, while the power supply 114 of the electronics module 102 may be a battery, the power supply 126 for the external monitor 104 may include an AC power supply that is supplemented with a rechargeable battery to enable the external monitor 104 to operate seamlessly between being plugged into a wall socket and being moved throughout a hospital until it can be eventually be plugged back into a wall socket.

For purposes of this invention, the GUI 122 further includes human interface devices that enable interaction with the GUI 122 such as but not limited to virtual or physical keyboards, touchscreens, joysticks, control pads and the like. Accordingly, use of the GUI 122 in conjunction with the display 124 enables user input to the system 100 and further allows selection or customization of what is shown on the display 124. The GUI 122 in conjunction with the communication module 116 and the communication module 108 further enables settings on the electronics module 102 to be manipulated or adjusted to optimize output from the system 100. Similarly, the GUI 122 enables user input to the processor 118 or the memory 120 to enable input and adjust settings that are applied to data from the sensor array 101 to determine a risk factor for heart failure.

The system further optionally includes a mobile device 128 having a user interface, such as, but not limited to a smartphone, a mobile phone, a smartwatch, a laptop, an ultrabook, a tablet computing device, a pager, and the like. The mobile device 128 is configured to receive data from the electronics module 102 via at least one of the cloud 106, the external monitor 104, or the electronics module 102 itself. In many embodiments the mobile device 128 is in bidirectional communication with the electronics module 102 that enables input via the user interface of the mobile device 128 to be transmitted to the electronic module 102. This enables a user of the mobile device 128 to manipulate, configure, or program settings on the electronics module 102. In some embodiments, bidirectional communications enables processing of data from the sensor array 101 on the mobile device 128. Additionally, in embodiments where the mobile device 128 includes a display, real time data and trends derived from the data is shown on the mobile device 128. In embodiments where the mobile device 128 includes at least one of an audible, tactile and visual alarm, the mobile device 128 can be used to update users of the mobile device 128 of the status of a patient wearing the sensor array 101. The status of the user includes, but is not limited to whether the system 100 is functioning properly, faults within the system 100, or real time measurements from the sensor array 101.

Another optional component within the system 100 is the cloud 106. Generally, the cloud 106 is considered a type of cloud computing that can be generalized as internet based computing that provides on demand shared computing processing resources and data to computer and other internet connected devices. In some embodiments the cloud 106 receives data from the electronics module 102 directly. In other embodiments data from the electronics module is transmitted to the mobile device 128 before being transmitted to the cloud 106. In still other embodiments, the cloud 106 receives data from the electronics module 102 via the external monitor 104. In still other embodiments, various permutations of communications initiated by the electronics module and transmitted between the external monitor 104 and the mobile device 128 results in data being transmitted to the cloud 106.

Data received by the cloud 106 may have already been processed by an intermediary device or can be processed on the cloud 106 and transmitted back to the intermediary device. In some embodiments, the cloud 106 contains electronic medical records and data from the sensor array 101 is automatically uploaded to the electronic medical records. With real time data being uploaded to the cloud, it becomes possible to apply machine learning which can further enable automatic or semi-automatic adjustments to the electronics module 102. Automatic updating would result in changes to the programming of the electronics module without human intervention whereas semi-automatic updating would require someone to confirm changes to the programming of the electronics module 102. In one example, the cloud 106 enables examination of medical history such as pre-existing conditions and family history and machine learning can suggest or set customized thresholds and sensor sampling rates based on previous data from patients with similar conditions and data The previously discussed components or elements within the system 100 are intended to be exemplary rather than limiting. As the system is intended to be flexible components are able to be added and removed based on immediate needs. This includes enabling or disabling system components within one environment while enabling or disabling the same system components at a later point.

Determining the Risk Score—Processing Sensor Data

Figure 7:
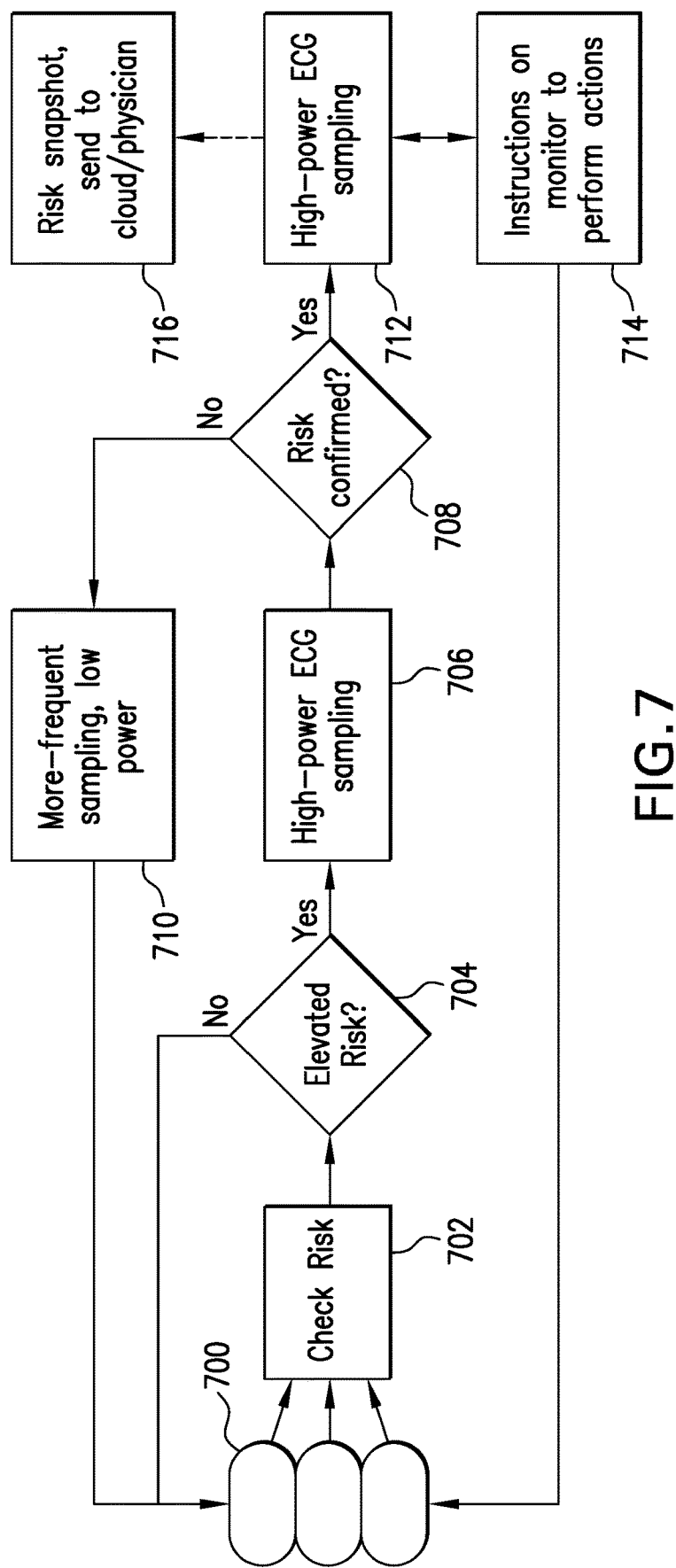
FIG. 7 is an exemplary flowchart illustrating operations performed by various components of the system while determining a risk score for heart failure in an interactive mode for an ambulatory subject, in accordance with embodiments of the invention.

FIG. 7 is an exemplary flowchart illustrating operations performed by various components of the system 100 while determining a risk score for heart failure in an interactive mode for an ambulatory subject, in accordance with embodiments of the invention. The flowchart begins with operation 700 that collects data from the sensor array 101. In some embodiments, operation 700 is performed while the system is in a low power operating mode that passively collects data from the sensor array such as, but not limited to heart rate, tissue oxygen levels and concentration of ROS/ORP. In other embodiments low power operation includes either or both measurements of tissue impedance and ECG at relatively long periodic intervals. Operation 702 utilizes the data acquired in operation 700 to determine a risk score for developing heart failure. Operation 704 determines if the risk score determined in operation 702 is elevated. In some embodiments various threshold levels can be set to define when a risk score is elevated. In other embodiments, threshold levels for an elevated risk score are predetermined and are not user configurable. If operation 704 determined the risk score is not elevated, the flowchart returns to operation 700.

If operation 704 determines the risk score is elevated, operation 706 begins operating the system in a high-power ECG sampling mode. High-power ECG sampling mode begins sampling ECG data at a higher frequency that may have been sampled during low-power operation. Operation 708 confirms if data acquired while using high-power mode confirms the elevated risk determined when using low-power mode. If the elevated risk is not confirmed, operation 710 returns the system to low-power operation while increasing the sampling rate of ECG data. If operation 708 confirms the elevated risk operation 712 continues high-power ECG sampling. While operating in high-power ECG sampling mode optional operation 714 provides instructions on a display for the subject to perform additional actions. In many embodiments the additional actions include, but are not limited to have the subject walk, stand, sit, lie down, and/or touch an skin contacting electrode on the exterior of the sensor assembly and the like. While the subject is performing the additional actions the system would operate in high-power mode acquiring ECG data. In embodiments where the system is connected to the cloud or other online data systems, operation 716 creates a risk snapshot that can be sent to the electronic medical records for a subject or to a subject's physician of choice.

In other embodiments, the system 100 operates in an active monitoring mode. The active monitoring mode may be more appropriate for hospital environments and enables more frequent sampling of ECG data. In many embodiments of active monitoring mode, it may already be known that the subject has an elevated risk profile that enables the system to optionally bypass the low-power mode described above regarding interactive mode. However, even in active monitoring mode, additional interactions may still be requested if additional data is required for pathological diagnosis or determination of a risk score.

The particular operating modes described above are intended to be exemplary and should not be construed as limiting. Additional embodiments different than those described above can encompass various other operational protocols and sensors that enable additional or fewer features. Additionally, the operations described above should not be construed as having to be performed in any particular order insofar as the operations can be reordered without compromising functionality of the system.

FIGS. 8A-8H are various exemplary illustrations of what can be presented on a display 124 or mobile device 128 (FIG. 1), in accordance with embodiments of the present invention. In most embodiments the display is the primary method of providing feedback to the subject being monitored. Data acquired by the sensor array may be periodically streamed or uploaded to a care partner or clinician, however in an ambulatory setting, the display or mobile device application enables a subject to view their current and past states. Accordingly, embodiments of a mobile application or hospital monitor should enable a daily review of risk factors that are individual components of the risk score. Additionally, viewing of instantaneous data from the sensor array, along with review of historical data should also be enabled. Furthermore, the application or display should enable interactive self-checks as directed by a software application along with allowing freeform text entry for logging individual events. In preferred embodiments, the application/display will further enable contact sharing and/or real time data sharing with a care partner or clinician.

Figure 8B:
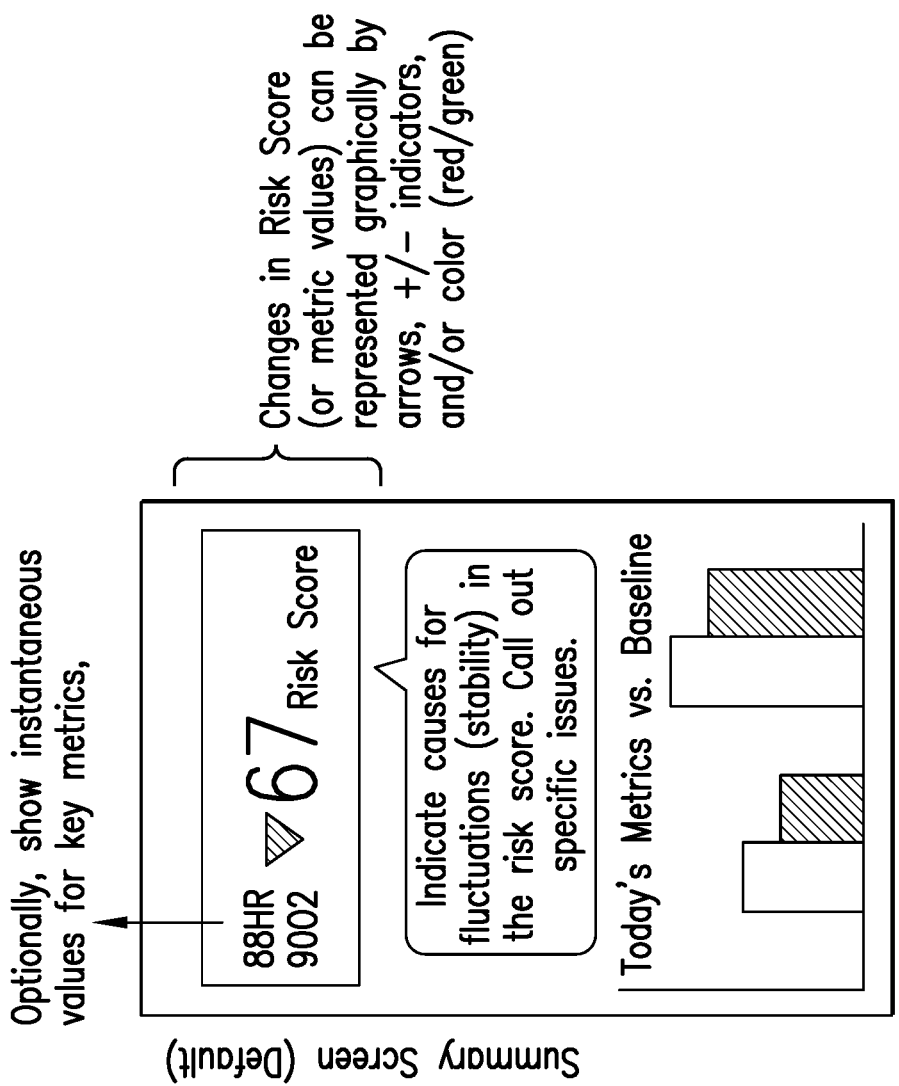
FIGS. 8A-8H are various exemplary illustrations of what can be presented on a display or mobile device, in accordance with embodiments of the present invention.
Figure 8A:
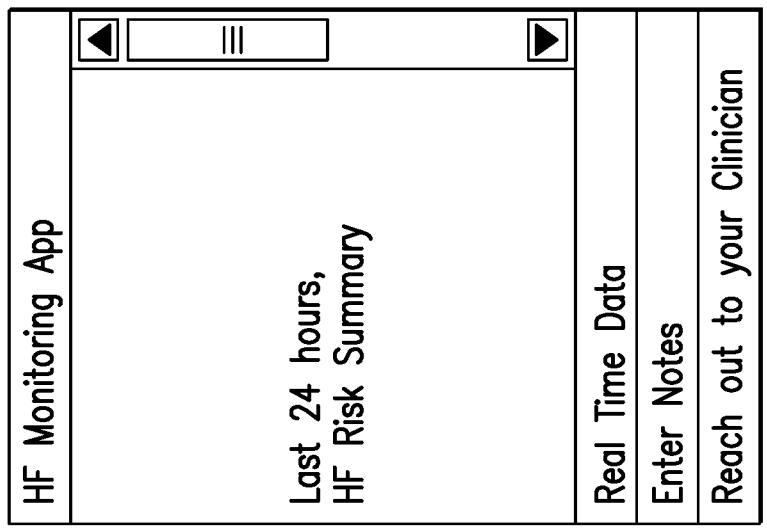

FIG. 8A is an exemplary illustration of a heart failure monitoring application showing default screens for monitoring a subject with the system 100. Input through a user interface allows selection to display different information such as, but not limited to realtime data or data acquired within a specified window. FIG. 8B is an example of a screen for a heart failure monitoring application that displays real-time data along with a risk score of developing heart failure. Various graphical elements such as, but not limited to, arrows and colors of arrows can be used to indicate trending information. Additionally, real-time metrics can be displayed concurrently with baseline or "ideal" values for the specified metric.

Figure 8D:
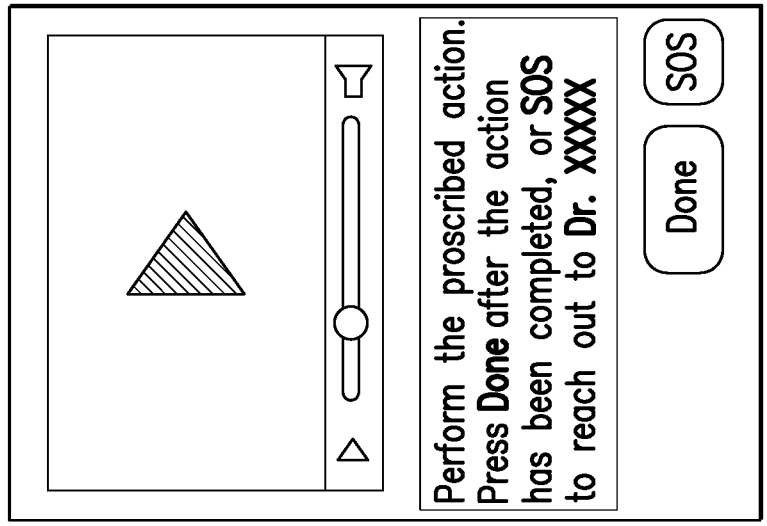
Figure 8C:
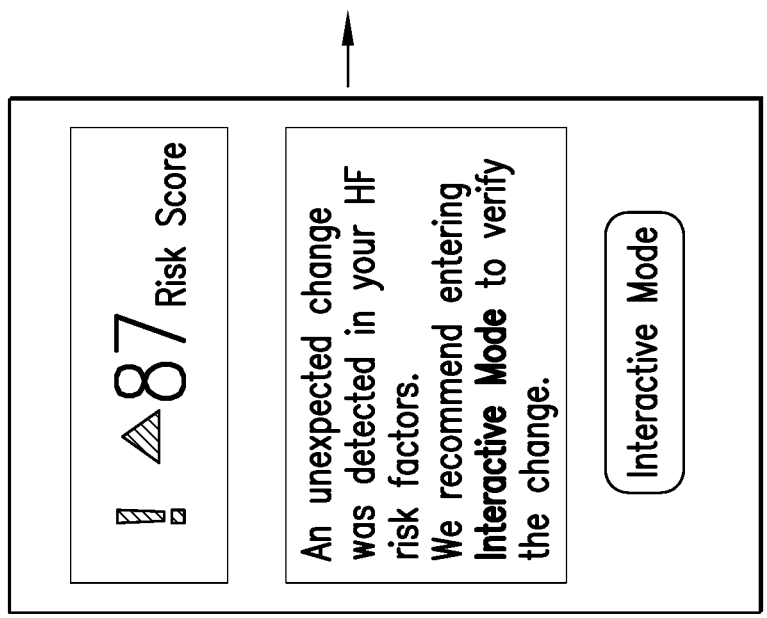

FIG. 8C is a non-binding, non-limiting sample mockup screen of a notification displayed to a user of the system 100. As illustrated the screen indicates an alert regarding the risk score and provides interactive instructions to enter an interactive mode. FIG. 8D is a sample screen of an interactive mode. In many embodiments, the interactive mode display videos or pictures of motions/actions that are intended to be performed by the user. Text and/or audible instructions can accompany the graphical instructions. In many embodiments, the interactive mode screens are modeled after troubleshooting screens/instructions associated with changing toner cartridges and clearing paper jams in photocopiers and printers.

The types of instructions provided in interactive mode may vary depending on the location of the sensor assembly on the subject. However, the overall goal of interactive mode is to have a subject perform specific physical tasks that enables refinement and/or confirmation of the risk score for heart failure. Non-limiting, exemplary interactive instructions would be for a subject to raise or lower their arms or legs a specified number of times within a specified time period. As the requested motions are being performed, accelerometers or other sensors within the sensor array can assist in confirming if the subject is actually moving and performing some, if not all the required movements. Throughout the time period to execute the instructions, the sensor array can further measure changes in within the microcirculation surrounding the sensor via changes in at least one of tissue oxygen levels, ROS, lactate or glucose. The particular physical task described above should not be construed as limiting. Other types of physical tasks include, but are not limited to forming and squeezing a fist multiple times, performing bicep curls, squatting and standing a specified number of times, stomach crunches, jumping jacks, and the like.

In many embodiments, various combinations of physical tasks may be requested. In addition to combinations of physical tasks, instructions may be provided to a user to take rest periods between physical tasks. Depending on the changes measured by the sensor array during and after the requisite physical task or tasks are performed, follow up physical tasks may be requested or additional input may be requested. For example, if additional data is required the system may remain in interactive mode and request additional different physical movement or repetition of previously executed physical movements. Alternatively, in some embodiments, especially those being used within a clinical environment, may request specific data from electronic health records or even data such as, but not limited to urine output, intravenous input, fluid consumption, meal times, estimated carbohydrates consumed and the like.

Because the system can be deployed in a wide variety of environments, such as, but not limited to the ones described above and throughout this disclosure, an additional feature of the system is the ability to adapt for patients or subjects that are utilizing an oxygen mask or whose therapy or condition requires the use of assisted ventilation. Regardless of whether the use of an oxygen mask or ventilator is the result of a clinical procedure or an unexpected event, in either case increasing inhaled oxygen should result in a measurable change in tissue oxygenation. In embodiments where tissue oxygen of a patient is being monitored prior to use of an oxygen mask or ventilator, if a change is not detected, or if the change is not sufficient, the system can utilize the data as a component in determination of a risk score. For patients already receiving oxygen or requiring ventilation, the tissue oxygen sensors can provide feedback regarding efficacy of therapy.

Figure 8F:
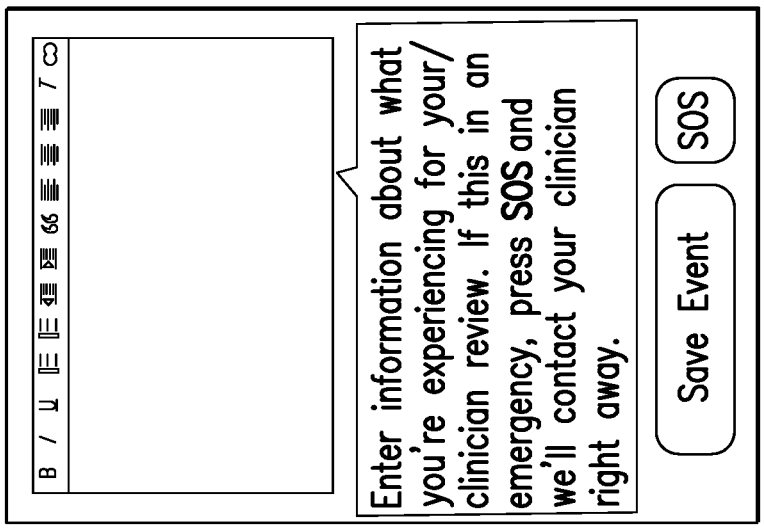
Figure 8E:
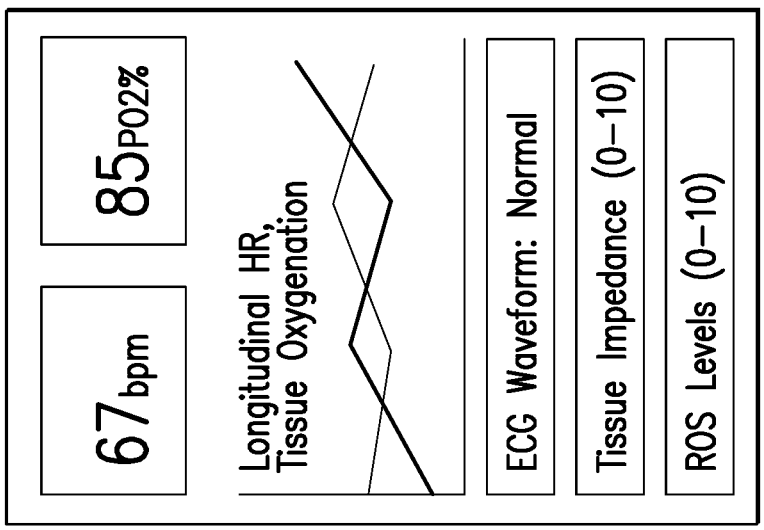

FIG. 8E is a sample screen illustrating how real-time data could be displayed while FIG. 8F shows an exemplary text entry screen to initiate or continue communication with a physician or care provider. In FIG. 8E, real-time data can be displayed in discrete numbers or graphically over time. Additionally, in some embodiments the user is allowed to select which metric or metrics are displayed. The communication screen shown as FIG. 8F is intended to allow a user to enter notes or initiate contact or continue ongoing communication with a physician, clinician or care provider. In some embodiments, text entry can be automatically sent as an email, SMS, or chat protocol such as, but not limited to iMessage, Google Allo, WhatsApp, Google Hangouts or the like. In still other embodiments, the communication screen further enables video chatting directly with a clinician, physician or caretaker using protocols such as, but not limited to Apple Facetime, Microsoft Skype, Google Hangouts, or Google Chat. In still other embodiments, the communications screen enables a user to contact emergency medical services while concurrently sending real-time data from the system along with a user's location via global positioning system (GPS) when available.

Figure 8G:
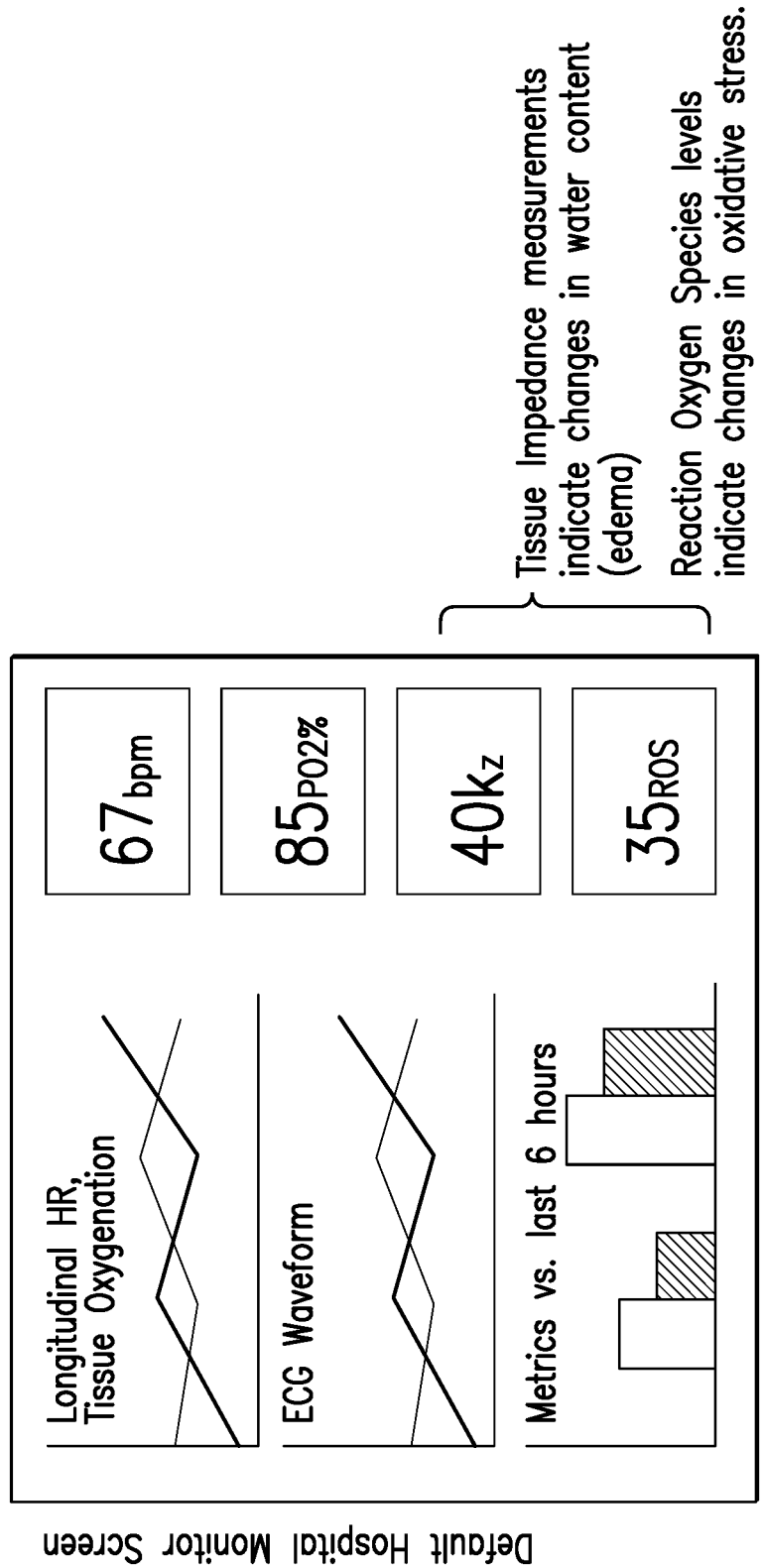
Figure 8H:
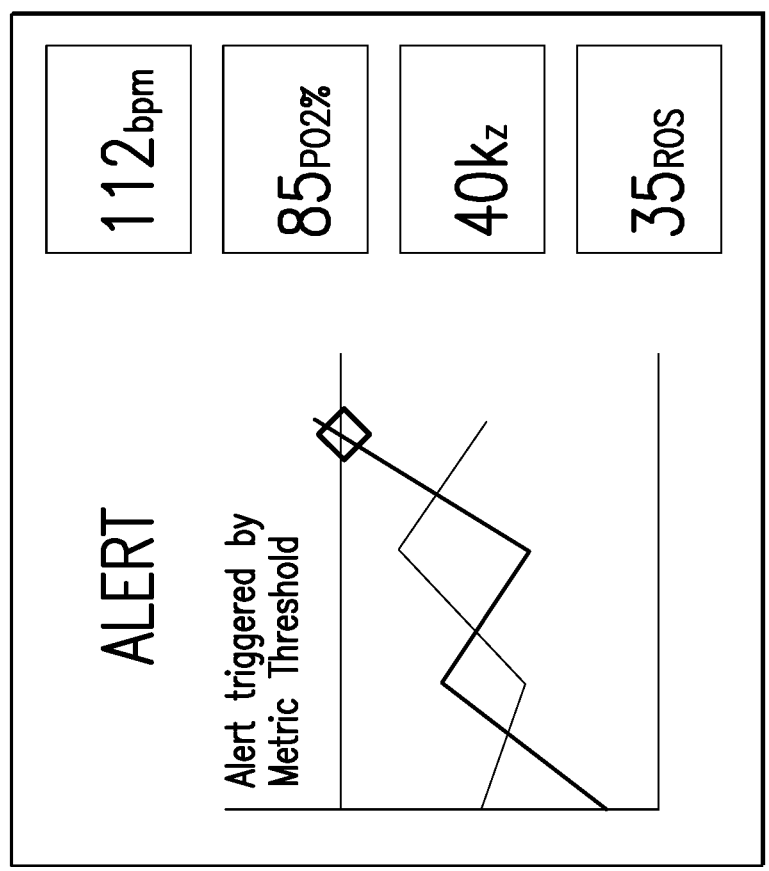

FIG. 8G is an example of a monitoring screen in a hospital environment while FIG. 8H is an example of an alert screen within a hospital environment. In both FIGS. 8G/8H, more technical displays are enabled that include various real-time sensor measurements for the clinical staff. For example, longitudinal view are available for ECG waveforms along with real-time and historical risk score values. Additional annotations such as trend indicators, target values and threshold values are optional available for display. In most embodiments of FIGS. 8G/8H, clinical staff are allowed to modify or configure which and in what format the various metrics are displayed. Furthermore, in clinician mode the monitor can be used to configure alerts and alarms that can be in the form of visual screen and/or audible tones. In some embodiments the alerts and alarms are effectuated locally at the monitor where they were configured. In other embodiments, attending physicians along with clinical staff can be notified via pager, SMS messaging or other proprietary communications protocol.

Figure 9:
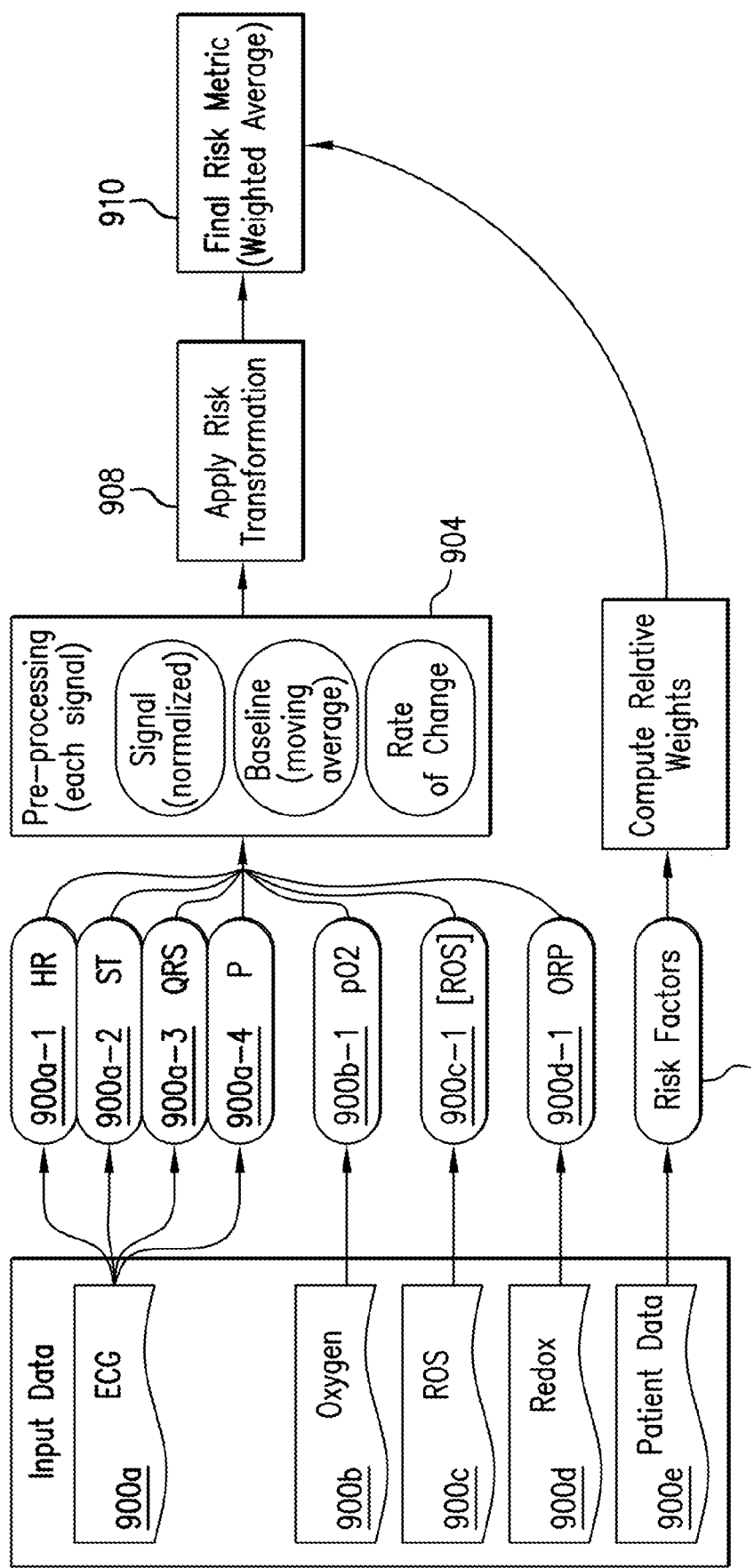
FIG. 9 is an exemplary block diagram illustrating how data from the sensor array is processed by a risk algorithm to determine a risk score of developing heart failure, in accordance with embodiments of the present invention.

FIG. 9 is an exemplary block diagram illustrating how data from the sensor array is processed by a risk algorithm to determine a risk score of developing heart failure, in accordance with embodiments of the present invention. The risk algorithm uses input data 900 that includes multiple parameters 900a-900e to assess a subject's risk for heart failure. The parameters included in FIG. 9 include measurements from the sensor array such as, but not limited to ECG data 900a, tissue oxygen 900b, ROS 900c and ORP 900d. Additionally, patient data 900e includes subject-specific demographic information (i.e. for high risk individuals, for those with pacemakers, etc). Patient data 900e can further include event-based inputs can also be handled the same way as demographic information (i.e. drug administration like blood thinners).

In preferred embodiments ECG data 900a is evaluated and transformed into secondary inputs such as, but not limited to, average heart rate (HR) 900a-1, ST segment (ST) 900a-2, QRS interval (QRS) 900a-3, and P-wave duration (P) 900a-4. Likewise, oxygen sensor data 900b can be transformed into partial pressure of oxygen (pO2) 900b-1 and ROS sensor data 900c can be transformed into an ROS/ORP ratio based on ROS 900c-1 and ORP 900d-1. Similarly, patient data 900e can be parsed for algorithm specific risk factors such as, but not limited to age, height, weight, and whether the patient smoke are non-limiting exemplary risk factors.

Pre-processor 904 pre-processes the input data and secondary data to provide optional data such as, but not limited to, a normalized signal, or a baseline value (longitudinal moving average), and/or rate of change (longitudinal). Risk transformation 908 applies risk transformations to the pre-processed metrics resulting in a normalized risk value [−1, 1] based on clinical standards for "safe" versus "risky" regions/values. The transformed risk values are combined into a final risk score 910 of heart failure via weighted average. In one embodiment, standard weights for patients with no preexisting conditions/unknown conditions would be provided. Weights can be modified automatically based on patient demographic data (preexisting condition, genetics, etc.). In addition, depending on the environment (e.g. operating room, intensive care unit, etc.) a clinician may decide to modify risk weights to tune sensitivity/specificity of the device.

In many embodiments, metrics are weighted based on a number of factors such as, but not limited to the correlation of a metric with heart failure and heart failure risk, discernable accuracy using the system, and capability to provide real-time information about the subject. For example, the average heart rate (HR) of a subject may be very heavily weighted because heart rate is a relatively easy diagnostic of heart failure. Additionally, heart rate can be obtained in real-time via the sensor array and its periodicity makes the signal readily processable. Similarly, ECG signals that directly measure the polarization of the chambers of the heart and its measurement directly measures the function of heart muscles. While ECG signals can provide more information than the simpler heart rate metric, particularly in a pathological sense, obtaining quality ECG signals may be more difficult because signal strength can depend on electrode orientation. An additional potential issue using ECG signals is that with more data to process (e.g., ST, QRS, and P) there is an increased potential for errors in measuring and processing the data. However, in many embodiments, the metrics of heart rate and ECG are given more weight in the risk algorithm because of the high correlation with heart failure and risk of developing heart failure.

FIGS. 10A-10D are exemplary illustrations of risk transformations in accordance with embodiments of the present invention. In many embodiments, risk transformations 908 are applied to pre-processed data Physiologically there are at least four types of transformations for the primary and/or secondary metrics. FIGS. 10A-10D illustrate risk increase in quadratic fashion versus input value, however these can be modified or augmented to be binary, or linear, or another higher-level transformation. Regardless of the type of transformation, the risk transformation should modeled to properly estimate risk for heart failure. Two exemplary considerations in how gradually risk should be modified include, but are not limited to clinical relevance and sensor accuracy, or reading specificity.

Clinical relevance can be understood by considering the deviation from "normal" physiological ranges. However, deviations from "normal" are typically not binary in nature thereby allowing for a gradual elevation in risk. However, in some cases a rapid "switch" in risk may be appropriate (i.e., detection of atrial fibrillation in ECG signals should immediately trigger a high risk warning). Sensor accuracy, or reading specificity can be considered regarding the ROS sensors. In some embodiments if there is a high level of background noise (poor selectivity for the target substrate i.e. H2O2), then risk may need to be more gradually compared to the standalone physiological ranges. Fortunately, this can be accounted for in the risk transformation and/or in the relative weighting to calculate the aggregate risk score.

In the embodiments described, oxygen, ROS and ORP are provided by real-time sensors. Changes in the peripheral concentrations of oxygen and ROS/ORP, away from the norm can be symptomatic of heart malfunction. Specifically, poor or low tissue oxygenation may be indicative of inefficient oxygen transfer via the circulatory system. Furthermore, changes or fluctuations in ROS and/or ORP may be suggestive of irregular stress or cellular death. However, note that changes in oxygen concentration are not necessarily a result of heart failure.

Figure 10A:
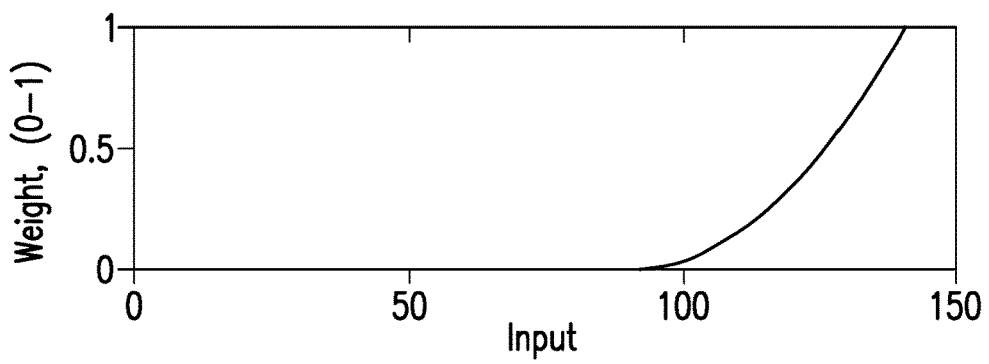
FIGS. 10A-10D are exemplary illustrations of risk transformations in accordance with embodiments of the present invention.
Figure 10B:
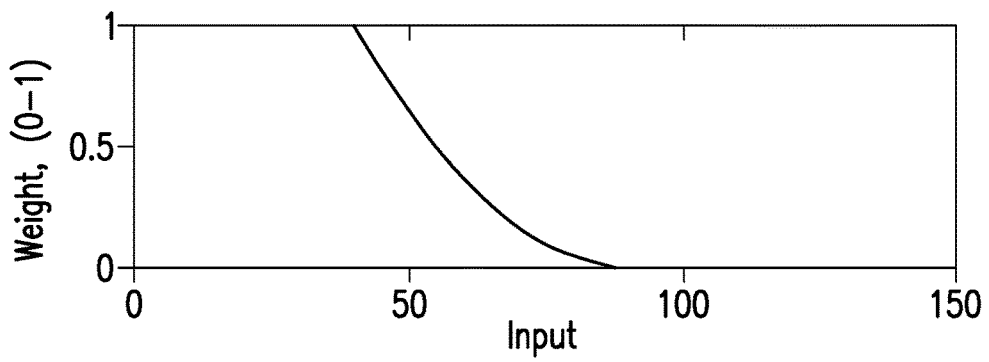
Figure 10C:
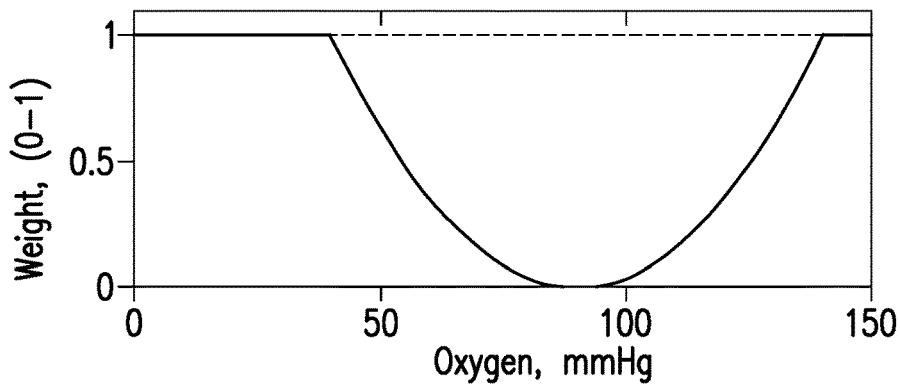
Figure 10D:
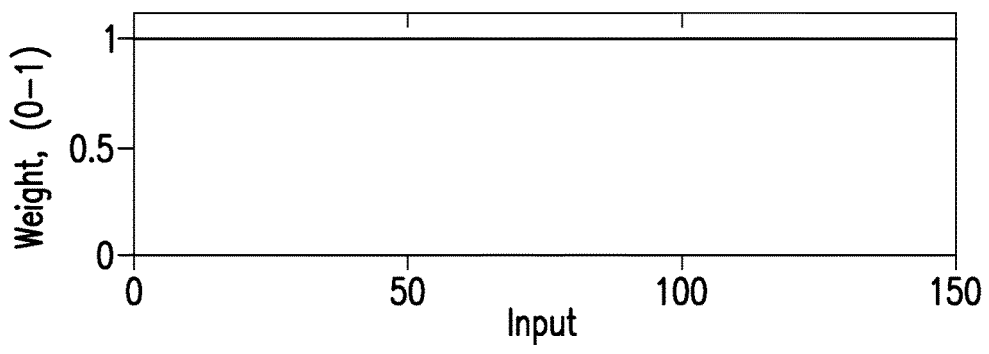

FIG. 10A is an exemplary illustration of a risk transformation where risk increases with increased signal. An example of a metric that may use the risk transformation shown in FIG. 10A could be ROS. FIG. 10B is an example of risk transformation where risk increase with decreasing readings. When determining a heart failure risk score a metric such as P-wave duration could use the risk transformation in FIG. 10B. Specifically, a low P-wave frequency could indicate atrial-ventricular blockage. This could be modeled as P-wave frequency (n events/second), or P-wave period (inverse, n seconds per event). FIG. 10C is an archetypal risk transformation for use where risk associated with a metric increases outside of an acceptable clinical range. Oxygen concentration is an exemplary metric where the risk transformation in FIG. 10C could be applied. FIG. 10D is a risk transformation for a metric where there is a constant risk. Exemplary metrics where a constant risk transformation could be applicable can be found in demographic information, such as, but not limited to age.

In various embodiments alerts and alarms are triggered by individual metrics crossing a specified threshold. For example, each of the secondary inputs can have at least one threshold value that will trigger an alarm or alert. For example, in one embodiments an alarm can be triggered if the average heart rate (HR) 900a-1 drops below 40. In many embodiments, predictive alerts are enabled using primary and secondary metrics in conjunction with rate of change data. An example of this type of alert would be based on a rapid increase in average heart rate. In still other embodiments, combinations of alerts and alarms can be used, such as, but not limited to an alarm that notifies a subject that there has been a rapid increase in average heart rate in addition to a low pO2. In still other embodiments, alarms and alerts can be configured based on the final risk metric 910 itself.

As previously discussed, the system is intended to be used in a variety of modes such as, but not limited to ambulatory monitoring, and remote monitoring each optionally supplemented by a feedback mode. Ambulatory monitoring mode is intended to either monitor progress of a patient previously diagnosed with heart failure or provide notification if a patient is potentially trending towards heart failure. The remote monitor mode is intended to leverage mobile technology and cloud based communications to provide early notification of the potential development of heart failure in high-risk patients away from traditional medical or care facilities. An additional mode, referred to as display mode, is to simply display and optionally record data from the sensor array on a display. The particular embodiments discussed above are exemplary embodiments of the system and should not be construed as the explicit limits of the system.

Other embodiments of the invention include separately or together, both detection and disease management based on continuous real time monitoring of multiple analytes indicative of disease states or medical conditions. For example, the system is adaptable to monitor the effectiveness of treatments such as, but not limited to chemotherapy. As many types of cancer are known to produce hypermetabolic activity within close proximity of a tumor, real time monitoring of metabolic activity near the tumor can provide insight of the efficacy of treatment. Similarly, the system is further adaptable to provide real time measurements and monitoring of analytes that are indicative of metabolic conditions and disease states associated therewith.

In addition to monitoring efficacy of cancer therapy and treatments, embodiments of the invention can also be used to monitor for conditions indicative of cancer in light of the following pathophysiological for some types of cancer. High energy metabolites such as ketones and lactate are associated with accelerated tumor growth and tumor metastases. Furthermore, increases in anabolic tumor growth rates are associated with upregulated mitochondrial metabolism that often are the byproduct of increases in circulating oxygen. Unique to behavior of cancer cells is the so called Warburg effect that describes the increased conversion to glucose to lactate even in the presence of normal to high levels of circulating oxygen. The energetically inefficient nature of the Warburg effect drives increases in glucose uptake through signaling pathways that ultimately leads to increases in insulin resistance and a concomitant increase in circulating glucose. The complex interplay amongst metabolic pathways associated with cancer cells suggest a continuous monitor capable of measuring ketones, oxygen, glucose, and lactate can be used to monitor those at risk for cancer, those who are being treated for cancer, and those who are at risk for cancer recurrence.

The continuous measurement of metabolites, their rates of change, and their relative concentrations can be analyzed through algorithms that serve to simulate or model the pathophysiological processes associated with tumor or cancer cell growth in order to identify individuals whose cancer risks have markedly increased and to then alert members of the care team through wired or wireless communication methods who can then initiate the appropriate intervention. A cancer monitoring system such as the one described above can also be used to monitor the effectiveness of a range of treatments and may in fact be used to enable more effective continuous treatment as opposed to the episodic or periodic protocols that tend to be reactive and as a result less effective in regards to treatment efficacy.

In embodiments not associated with metabolic conditions, the system is configurable to measure reactive oxide molecules such as, but not limited to nitric oxide and superoxide. As part of the body's inflammation response reactive oxide molecules are often overexpressed. Overexpression of reactive oxide molecules can cause the disruption of processes in the mitochondria and may have a role in mitochondrion dysfunction. Monitoring or detecting reactive oxide molecules and superoxide in relation to inflammation can be valuable within a hospital because of the strong indication for infection, regardless of patient profile.

While the specific embodiments discussed above are generally related to implantable probes or sensors, other embodiments can use non-invasive sensors to obtain tissue oxygen levels, other analyte levels or concentrations, and tissue hydration. In these embodiments, ECG data can be obtained using a variety of methods that includes, but is not limited to measuring ECG data between a skin contacting electrode and a implanted (temporarily or otherwise) probe or between two separate skin contacting electrodes. In embodiments using a skin contacting electrode and an implantable probe, the probe may be specifically implanted to obtain ECG data or may alternatively assist in determining tissue hydration. In the various embodiments discussed throughout this disclosure it is intended that features in each of the various embodiments can be combined or even separated where possible for the broadest possible configurations and embodiments.

Accordingly, while the description above refers to particular embodiments of the invention, it will be understood that many modifications may be made without departing from the spirit thereof. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

The invention claimed is:

1. A biosensor assembly measuring multiple parameters, comprising:
    a skin contacting surface that includes a first skin contacting electrode being located on a bottom of the biosensor assembly; and
    a first implantable probe extending away from the skin contacting surface, the first implantable probe being inserted through skin of a subject, the first implantable probe enabling signaling within subcutaneous tissue with a first working electrode and a second working electrode;
    wherein the biosensor assembly is configured to measure a first physiological parameter between the first implantable probe and the first skin contactable electrode, the first physiological parameter being tissue impedance measured between the skin contacting electrode and either the first or second working electrode of the first implantable probe within subcutaneous tissue.

2. The biosensor assembly as described in claim 1, wherein the first implantable probe measures a second physiological parameter independent of the first skin contacting electrode.

3. The biosensor assembly as described in claim 2, wherein the first implantable probe measures a third physiological parameter independent of the first skin contacting electrode.

4. The biosensor assembly as described in claim 2, further comprising: a second implantable probe inserted into subcutaneous tissue redundantly measuring the second physiological parameter independent of the first skin contacting electrode and the first implantable probe.

5. The biosensor assembly as described in claim 2, wherein the first implantable probe measures a first plurality of physiological parameters independent of the first skin contacting electrode.

6. The biosensor assembly as described in claim 1, wherein placement of the first skin contacting electrode against skin enables automated periodic measurements of the first physiological parameter.

7. The biosensor as described in claim 1, further comprising a second implantable probe being inserted into subcutaneous tissues, the first physiological parameter being redundantly measured between the second implantable probe and the first skin contacting electrode.

8. The biosensor as described in claim 1, wherein the first implantable probe includes electrodes on both an A-side and a B-side.

9. The biosensor as described in claim 8, wherein measuring the first physiological parameter is measured between electrodes on both the A-side and B-side of the first implantable probe and the first skin contacting electrode.

10. The biosensor as described in claim 8, wherein measuring the first physiological parameter is measured between electrodes on either the A-side or the B-side, of the first implantable probe and the first skin contacting electrode.

* * * * *